United States Patent [19]
Cave et al.

[11] Patent Number: 5,970,463
[45] Date of Patent: Oct. 19, 1999

[54] MEDICAL CLAIMS INTEGRATION AND DATA ANALYSIS SYSTEM

[75] Inventors: Douglas G. Cave, Chesterfield; Bradley Munson, Creve Couer, both of Mo.

[73] Assignee: Practice Patterns Science, Inc., Maryland Heights, Mo.

[21] Appl. No.: 08/641,556

[22] Filed: May 1, 1996

[51] Int. Cl.⁶ ............................................... G06F 159/00
[52] U.S. Cl. ........................................ 705/3; 705/2; 705/1
[58] Field of Search .................................... 705/2, 3, 4, 6

[56] References Cited

U.S. PATENT DOCUMENTS

| | | | |
|---|---|---|---|
| 4,489,387 | 12/1984 | Lamb et al. | 395/200.67 |
| 4,491,725 | 1/1985 | Pritchard | 705/2 |
| 4,667,292 | 5/1987 | Mohlenbrock et al. | 705/2 |
| 4,858,121 | 8/1989 | Barber et al. | 705/2 |
| 4,878,175 | 10/1989 | Norden-Paul et al. | 705/2 |
| 4,937,743 | 6/1990 | Rassman et al. | 705/8 |
| 4,987,538 | 1/1991 | Johnson et al. | 705/2 |
| 5,001,630 | 3/1991 | Wiltfong | 705/3 |
| 5,018,067 | 5/1991 | Mohlenbrock et al. | 364/413.02 |
| 5,065,315 | 11/1991 | Garcia | 705/2 |
| 5,070,452 | 12/1991 | Doyle, Jr. et al. | 705/2 |
| 5,072,383 | 12/1991 | Brimm et al. | 705/2 |
| 5,099,424 | 3/1992 | Schneiderman | 705/3 |
| 5,235,702 | 8/1993 | Miller | 707/102 |
| 5,253,164 | 10/1993 | Holloway et al. | 705/2 |
| 5,301,105 | 4/1994 | Cummings, Jr. | 705/2 |
| 5,307,262 | 4/1994 | Ertel | 705/2 |
| 5,319,543 | 6/1994 | Wilhelm | 705/3 |
| 5,325,293 | 6/1994 | Dorne | 705/2 |
| 5,359,509 | 10/1994 | Little et al. | 705/2 |
| 5,392,209 | 2/1995 | Eason et al. | 707/3 |
| 5,404,292 | 4/1995 | Hendrickson et al. | 600/301 |
| 5,467,268 | 11/1995 | Sisley et al. | 705/9 |
| 5,471,382 | 11/1995 | Tallman et al. | 600/300 |
| 5,483,443 | 1/1996 | Milstein et al. | 705/3 |
| 5,486,999 | 1/1996 | Mebane | 705/2 |

(List continued on next page.)

OTHER PUBLICATIONS

Bell, Nancy N. 1994. "Hedis: Are We Finally Comparing Apples to Apples?" *Medical Interface*, 7, No. 4: 74–6, 81–2.

Boyer, N. 1993. "Software Solutions for Health Care Challenges," *Journal of Health Care Benefits*, 2, 33–7.

Brosgol, Franklin L., M.D. 1996. "Data Integration: Blue Skies Ahead for Network Management," *Medical Interface*, 9, No. 1:85–8.

(List continued on next page.)

*Primary Examiner*—Kevin J. Teska
*Assistant Examiner*—Matthew Loppnow
*Attorney, Agent, or Firm*—Bryan Cave LLP

[57] ABSTRACT

A medical claims analysis system and method categorizes medical claims into episodes of care having predetermined diagnostic cluster types. The system analyzes medical claim items, some of which have principal diagnosis codes, and some of which have non-principal, missing, or incorrect diagnosis codes. Patient treatment episodes (PTEs) are formed from the principal diagnosis codes, each PTE being of a particular diagnostic cluster type. The system categorizes non-principal-diagnosis claim items into the PTEs on the basis of temporal, physiological or clinical relationships between the claim items and the PTEs. A drug lookup table enables drug claims to be properly categorized in the PTEs. A diagnostic cluster lookup table enables claim items to be categorized into PTEs with ongoing treatment windows for which the diagnosis code of the claim item is in the diagnostic cluster lookup table. The system merges PTEs of the same diagnostic cluster type when the treatment windows of the PTEs overlap. The system attempts to recategorize medical claims into merged PTEs. The system analyzes each PTE to determine the presence of required diagnoses and eliminates any PTE without a required diagnosis. The system also identifies and merges PTEs that are clinically related or clinically similar. In a system for integrating medical claims data, medical claim items that are in different data formats and/or use different coding systems are analyzed, and related claim items are categorized in a common coding system.

41 Claims, 6 Drawing Sheets

U.S. PATENT DOCUMENTS

| | | | |
|---|---|---|---|
| 5,519,607 | 5/1996 | Tawil | 364/401 |
| 5,557,514 | 9/1996 | Seare et al. | 364/401 |
| 5,583,758 | 12/1996 | McIlroy et al. | 395/202 |
| 5,664,207 | 9/1997 | Crumpler et al. | 705/3 |
| 5,724,379 | 3/1998 | Perkins et al. | 395/202 |
| 5,835,897 | 11/1998 | Dang | 705/2 |

OTHER PUBLICATIONS

Cave, Douglas G., Ph.D., MPH. 1993. "Controlling Increases in the Volume and Intensity of Medical Services," *Employee Benefits Journal*, Jun.: 11–8.

Cave, Douglas G., Ph.D., MPH. 1994. "Analyzing the Content of Physicians' Medical Practices," *J Ambulatory Care Manage*, 17(3): 15–36.

Cave, Douglas G., Ph.D., MPH. 1994. "Small–Area Variations in Patterns of Treatment For Prevalent Medical Conditions," *Group Health Institute Proceedings*, 44: 927–49.

Cave, Douglas G., Ph.D., MPH & Geehr, Edward C., M.D. 1994. "Analyzing Patterns–of–Treatment Data to Provide Feedback to Physicians," *Medical Interface*, 7(7):117–27.

Cave, Douglas G., Ph.D., MPH. 1994. "Pattern–of–Treatment Differences Among Primary Care Physicians in Alternative Systems of Care," *Benefits Quarterly*, 10(3):6–19.

Cave, Douglas, G., Ph.D., MPH. 1992. "Evaluating Health Plan Efficiency," *Compensation & Benefits Management*, 8 (3).

Cave, Douglas G. Ph.D., MPH. 1995. "Using Diagnostic Clusters to Evaluate Patterns of Treatment and Develop Capitation Rates," *Employee Benefits Journal*, 20(1):24–30.

Cohen, Kenneth R. & Naughton, Diane H. 1995. "Patient–Centered Care: A Revolution in Medicine," *Medical Interface*, 8, No. 6:66–73.

Dang, Dennis K., M.D., Pont, Jeffrey M., M.D. & Portnoy, Mitchell A., MPH. 1996. "Episode Treatment Groups: An Illness Classification and Episode Building System—Part 1," *Medical Interface*, 118–22.

Dang, Dennis K., M.D., Pont, Jeffrey M., M.D. & Portnoy, Mitchell A., MPH. 1996. "Episode Treatment Groups: An Illness Classification and Episode Building System—Part 2," *Medical Interface*, 122–28.

Federal Information Systems Corporation; Federal News Services. 1995. "Prepared Testimony of Value Health Science, Inc. to the Senate Committe on Appropriations Subcommitte on Labor, Health, and Human Services on Potential Savings to Medicare From Private Sector Technology."

Fetter, R., Averill, R., Lichtenstein, J. et al. 1984. "Ambulatory Visit Groups: A Framework for Measuring Productivity in Ambulatory Care," *Health Services Research*, 19, 415–37.

Fetter, R., Shin, Y., Freeman, J. et al. 1980. "Case Mix Definition by Diagnosis–Related Groups," *Medical Care*, 18, 1–53.

Goldfarb, Stanley, M.D., 1995. "Proving the Link Between Outcomes and Resource Utilization," *Medical Interface*, 8, No. 9:79–82, 84.

Kaurene, Bruce. 1993. "Using Clinical Knowledge to Enhance the Capture and Analysis of Medical Claims Data," *Medical Interface*, 6, No. 8:50–2.

Peskin, Steven R., M.D., 1994. "Merging the Medical and Pharmacy Databases: Barriers and Implications," *Medical Interface*, 7, No. 12:51–2.

Schneewiess, Ronald, M.B.Ch.B., Cherkin, D., Hart, L., et al. 1986. "Diagnosis Clusters Adapted for ICD–9–CM and ICHPPC–2," *Journal of Family Practice*, 22, 69–72.

Schneewiess, Ronald, M.B.Ch.B., et al., 1983. "Diagnostics Clusters: A New Tool for Analyzing the Content of Ambulatory Medical Care," *Medical Care*, 21, No. 1:105–22.

Sylvestri, Mario F., Pharm.D., Ph.D. 1996. "Health Care Informatics: The Key to Successful Disease Management" *Medical Interface*, 9, No. 5:94–6, 98–9.

Symmetry Health Data Systems, Inc. 1994. "Episode Treatment Groups Whitepaper."

Weiner, J.P., Starfield, B.H., Steinwachs, D.M., et al., 1991. "Development and Application of a Population–Oriented Ambulatory Care Case–Mix," *Medical Care*, 29, 452–72.

MEDICAL CLAIMS INTEGRATION AND DATA ANALYSIS SYSTEM

BACKGROUND OF THE INVENTION

1. Field of the Invention

The present invention relates generally to a method of and apparatus for analyzing medical claims data, and more particularly to a method of and apparatus for integrating medical claims data, including, inpatient, outpatient, ambulatory, clinical laboratory, and prescription drug claim data, from one or more sources for comparative analysis at the network level, provider level, or patient level. The invention organizes the claims into clinically related diagnostic clusters, and enables claims with missing or incorrect diagnostic codes to be categorized into such diagnostic clusters in order to better estimate the overall cost of patient treatment and to measure the efficiency of treatment at various levels.

2. Description of the Related Art

The costs of health care today are rapidly increasing as the health care industry becomes more complex, specialized and sophisticated. Over the years, the delivery of health care services has shifted from local physicians to large managed health care organizations. This shift reflects the growing number of medical specialties, and the complexity and variety of health care options and programs. This complexity and specialization has created large administrative systems that coordinate the delivery of health care between health care providers, administrators, patients, payers and insurers. The cost of supporting these administrative systems has been steadily rising, contributing to today's rising costs of health care.

Beginning in the late 1970's, the precipitous increase in medical care costs prompted health insurance companies to evaluate insurance claims data to determine the reasons behind this increase. The first-generation claims data evaluation systems that were developed generally concentrated on analyzing medical charges and utilization in the hospital inpatient setting. As a result of these evaluations, health insurers implemented pre-certification utilization review programs to control unnecessary inpatient admissions and days, and employers turned to preferred provider organizations to manage per-day charge increases.

First-generation data claims analysis, however, was short lived. After Medicare implemented the Prospective Payment System (PPS) in 1983, the number of hospital in-patient days significantly decreased for both the Medicare and non-Medicare populations. The PPS provided physicians with financial incentive to treat certain patients in an ambulatory setting. As more health care dollars were spent on ambulatory services, employers and health insurers realized that both hospital and ambulatory treatment had to be evaluated to determine the principal reasons for health care cost increases. Thus, insurance carriers and consultants developed second-generation data analysis systems focusing on ambulatory utilization and charges.

Most second-generation data claims analysis systems currently evaluate utilization experience on a basis of per-1,000-covered-individuals (i.e., employees and their dependents) and charges on a per-service basis. For example, common utilization rates include the number of hospital admissions, physician office visits, and prescription drug fills per 1,000 individuals. Charge rates consist of charges per hospital day, per X-ray/diagnostic testing service, and per physician office visit.

Using second-generation systems, gross overutilization and significant excess charge patterns can be identified in both hospital and ambulatory care settings. For instance, if the number of prescription drugs prescribed per 1,000 covered individuals is 50 percent greater than an expected value, the health network can be reasonably sure that it has a problem with prescription drug utilization. For various reasons, however, these second-generation systems are not very accurate at assessing a health plan's overall cost efficiency. By cost efficiency is meant that a plan's overall providers treat medical conditions with the least expensive level of medical care possible and still achieve the desired health outcome for the patient.

Second-generation systems generally do not combine and evaluate all hospital and ambulatory services incurred for treating an individual's medical condition. Instead, these systems divide individual's claims into 20 to 25 different utilization and charge categories. Each category is then analyzed separately to determine whether there is a problem with utilization per 1,000 individuals, charges per service, or both. If problem areas are identified, health care networks develop specific cost-control strategies to contain future benefit increases.

This process, however, is a piecemeal approach for evaluating the cost efficiency of a health plan, and health care networks may draw wrong conclusions from such an analysis. For example, assume that a network determines that the number of physician office visits per 1,000 individuals is 30 percent higher than an expected value. A logical conclusion is that the health plan's physicians are not practicing cost-efficient medicine. Yet if the health plan observes that the number of hospital admissions is 20 percent lower than expected, a different conclusion may be reached: perhaps, for example, physicians are practicing cost-efficient medicine by treating patients in the ambulatory setting whenever possible. The health plan must then make a subjective assessment as to whether a 30 percent higher-than-expected physician office visit rate is acceptable or too high given the low hospital admission rate.

Consequently, a need exists for a system to enable health care networks to analyze their medical claims/encounter data and to more accurately evaluate the overall cost efficiency of the health plan at the network level, at the provider level, and at the patient level.

The American Medical Association in conjunction with the Health Care Financing Administration developed a system of codes for the purpose of describing physician work for medical and surgical procedures, diagnostic tests, laboratory studies, and other physician medical services rendered to clients. This system of codes is generally referred to as Current Procedural Terminology, or CPT, codes. They provide a uniform language that details medical, surgical, and diagnostic services utilized by physicians to communicate to third-party payers the services that are rendered.

The World Health Organization developed a similar method to identify diseases, injuries, impairments, symptoms, medical procedures and causes of death. These codes are International Classification of Diseases 9th edition Clinical Modification (ICD.9) codes. The ICD coding system was designed for the classification of morbidity and mortality information for statistical purposes and for the indexing of hospital records by disease and operations for data storage and retrieval. The ICD codes are initially divided into Disease and Procedure sections. These sections are further divided into subsections which encompass anywhere from 1–999 three digit disease or 1–99 two digit procedure code categories. Within the three digit code categories there can be an additional 1 or 2 decimal digits to divide the codes into subcategories which further define the disease manifestations and/or diagnostic procedures. There are approximately 15,000 ICD.9 codes. It will be appreciated that while the present invention will be described specifically with respect to ICD.9 coding, the invention is applicable to future versions of the ICD classification system, and may be modified to operate with other types of classification systems as well.

Billing for a physician's services has become increasingly more complex in recent years. Medicare requires that a code be assigned to each patient encounter, the interaction between a patient and the physician, assistant, nurse or other health care provider to evaluate the patient's medical problem. One problem that has arisen is that physician's may submit medical claims with improper or missing diagnosis codes. This makes it difficult in assessing overall treatment charges to include the charge data for those claims that are improperly coded. Accordingly, it would be desirable to have a system that organizes medical claims data into clusters in which all claims related to a medical condition, including those claims that are improperly coded and drug claims, are grouped so that it is possible to ascertain the overall costs of treating the medical condition.

Another problem that has arisen due to changes in the medical field is that of assessing the overall charges attributable to general physician's, who serve as gatekeepers to specialist services in HMO's. For example, assuming that a general practitioner treating a diabetic too often refers to patient to specialized care. Without attributing the charges of the specialist to the general physician, the overall costs for treating the patient that are attributable directly to the general physician will actually be lower than average, whereas if the charges of the specialist are included, the overall cost of treating the patient will be higher than average. Accordingly, it would be desirable to have a system that organizes medical claims data into clusters based upon the medical condition, and that enables all claims related to a medical condition to be attributable to a gatekeeper physician.

A further problem in assessing the overall costs of medical treatment is that certain claims, e.g., prescription drug claims, do not include ICD.9 codes. In some cases claims use alternative codings systems, such as GPI (Generic Product Identifier) codes, which are used to code prescription drug claims, and CPT codes. Accordingly, it would be desirable to have a medical claims analysis system that is capable of categorizing uncoded claims, or claims in alternative coding systems, with the ICD.9 coded claims related to treatment of the underlying medical conditions that necessitated the uncoded or alternatively coded claims.

Various systems have been patented in the medical billing field. Such systems are shown, for example, in U.S. Pat. Nos. 5,018,067; 5,359,509; 4,667,292; 5,483,443; 5,307, 262; and 5,253,164. None of these systems, however, overcomes the aforementioned problems with respect to assessing a health plan's true cost efficiency, assessing the overall costs of treatment of medical conditions, and allocation of medical costs to physicians to assess the efficiency of treatment by the physicians.

SUMMARY OF THE INVENTION

The present invention is a medical claims analysis system and method that enables a health plan to more accurately assess the plan's true overall cost efficiency and its cost efficiency with respect to treatment of particular medical conditions. The system categorizes medical claims into episodes of care as opposed to the "per 1,000 individuals" systems of the prior art. In using the episode-of-care approach, the system examines all services used to treat a patient's condition.

The medical claims systems includes a data storage device for storing medical claims data from one or more data sources. The medical claims data consists of medical claim items, at least one portion of which includes principal diagnosis codes, and at least a second portion of which includes non-principal diagnosis codes, no diagnosis codes, or incorrect diagnosis codes.

A data processing system forms patient treatment episodes ("PTEs"[1/]) from the principal diagnosis codes, each PTE being of a particular diagnostic cluster type. The data processing system categorizes at least some of the claim items of the second portion of medical claims in the PTEs on the basis of a relationship between the second portion claim items and the PTEs. The categorization is preferably performed on the basis of a temporal relationship between the claim items and the PTEs or on the basis of a physiological or clinical relationship between the claim items and the PTEs.

[1/] "PTE" is a trademark of Practice Patterns Science, Inc.

The second portion of the claims may include prescription and non-prescription drug claims. A drug lookup table is provided for relating prescription drugs to associated diagnostic cluster types. The data processing system preferably identifies the drug claims from the second portion of medical claims and identifies miscategorized drug claims using the drug lookup table. The drug claims may be recategorized into different PTEs, if appropriate. If desired, the drug lookup table may further relate drugs to associated diagnostic cluster types in more than one degree of preference. Drug claims may then be recategorized to PTEs based upon this degree of preference.

Each claim item preferably has an associated treatment date, and each PTE has a predetermined treatment window based upon its diagnostic cluster type. A diagnostic cluster lookup table is provided which associates each diagnostic cluster type with associated diagnosis codes. The second portion of claim items may be categorized into PTEs with ongoing treatment windows for which the diagnosis code of the claim item is associated with the diagnostic cluster type of the PTE in the diagnostic cluster lookup table. The diagnostic cluster types may be preference ranked with respect to diagnosis codes that are associated with more than one type of diagnostic cluster, and the claim items may be categorized in ongoing PTEs having the highest rank.

The system merges PTEs of the same diagnostic cluster type when the treatment windows of the PTEs overlap, thereby forming a merged PTE of the same diagnostic cluster type as the overlapping PTEs. The treatment window of the merged PTE extends from the date of the last treatment in the merged PTE. Once the merger has occurred, the system attempts to recategorize at least some of the second portion medical claims in the merged PTE on the basis of the treatment window of the merged PTE.

Some of the second portion of claims will normally have CPT codes associated therewith. The system includes a CPT lookup table for relating CPT codes to associated diagnostic cluster types. The system identifies CPT claims from the second portion of medical claims, identifies miscategorized CPT claims using the CPT lookup table, and recategorizes miscategorized CPT claims into different PTEs.

Some of the types of diagnostic clusters may have a required diagnosis associated therewith. The system analyzes each PTE to determine the presence of the required diagnosis and eliminates any PTE without the required diagnosis.

The system also includes the capability to identify PTEs that are clinically related or clinically similar, and links such clinically related or clinically similar PTEs. This feature enables the system to robustly deal with claims with missing or vague codes.

Each diagnostic cluster type also has a predetermined severity of illness relationship which relates a severity of illness to particular claim items in a PTE of that diagnostic cluster type. The severity of illness associated with each PTE is varied on the basis of the claim items in that PTE in accordance with the severity of illness relationship.

A system for integrating medical claim/encounter records includes:

A) data storage means for storing medical claims data, the medical claims data comprising medical claim items, each claim item having an associated treatment date, a first portion of the medical claim items comprising principal diagnosis codes;

B) means for forming initial patient treatment episodes (PTEs) from the principal diagnosis codes, each PTE comprising a predetermined treatment window extending from a last treatment in the PTE;

C) means for categorizing at least some of a second portion of the claim items into respective PTEs on the basis of a temporal overlap between the second portion claim items and the treatment windows of the PTEs and extending the treatment window for each respective PTE from the date of treatment of the second portion claim item categorized therein provided that such date of treatment is later than the prior last treatment in the PTE; and D) means for reanalyzing at least some of the second portion claim items and categorizing such claim items into respective PTEs on the basis of a temporal overlap between the second portion claim items and the extended treatment windows of the PTEs.

A system for integrating medical claims data, the system includes:

A) means for retrieving medical claims data comprising medical claim items related to treatment of a medical condition, the claims data being in more than one data format, each data format having a different coding system; and B) means for analyzing the medical claim items for categorizing related claim items using a common coding system.

DETAILED DESCRIPTION OF THE INVENTION

The present invention is a system for integrating medical claims/encounter records from multiple sources for comparative analysis thereof. As used herein, "medical claims/ encounter data" and "medical claims" may be used interchangeably, and include, but are not limited to: i) inpatient medical claims, which are generated during inpatient stays at hospitals or the like, and include all claims associated with a patient's stay in the hospital, e.g., room and board, prescription drug claims, medical tests, etc.; ii) outpatient medical data, which includes similar claims data generated during outpatient treatment; iii) ambulatory claims, which are generally for non-inpatient or outpatient physician visits and claims related thereto; and iv) miscellaneous claims data, including claims for prescription and non-prescription drugs, clinical laboratory tests, physical therapy, durable medical equipment, home health care, and other miscellaneous claims and/or services that are incurred in the health care field. Regardless of the type of medical claim, the claims data often includes missing or incorrect ICD.9 codes, especially for miscellaneous claims data such as prescription drugs.

When evaluating the medical claims/encounter data, the data may be located on one or more discrete computer systems and in different data formats. In order to be processed by the system of the invention, the data must be converted to a common data format and ported to a common computer system. The common computer system upon which the invention operates is preferably Unix-based, such as a DEC Alpha or an HP 9000. It will be appreciated, however, that the invention may be implemented on any appropriate computer systems. Moreover, those skilled in the art will appreciate that there are various techniques for conversion of the claims data to a common data format and for porting the claims data to a common processing computer.

Figure 1:
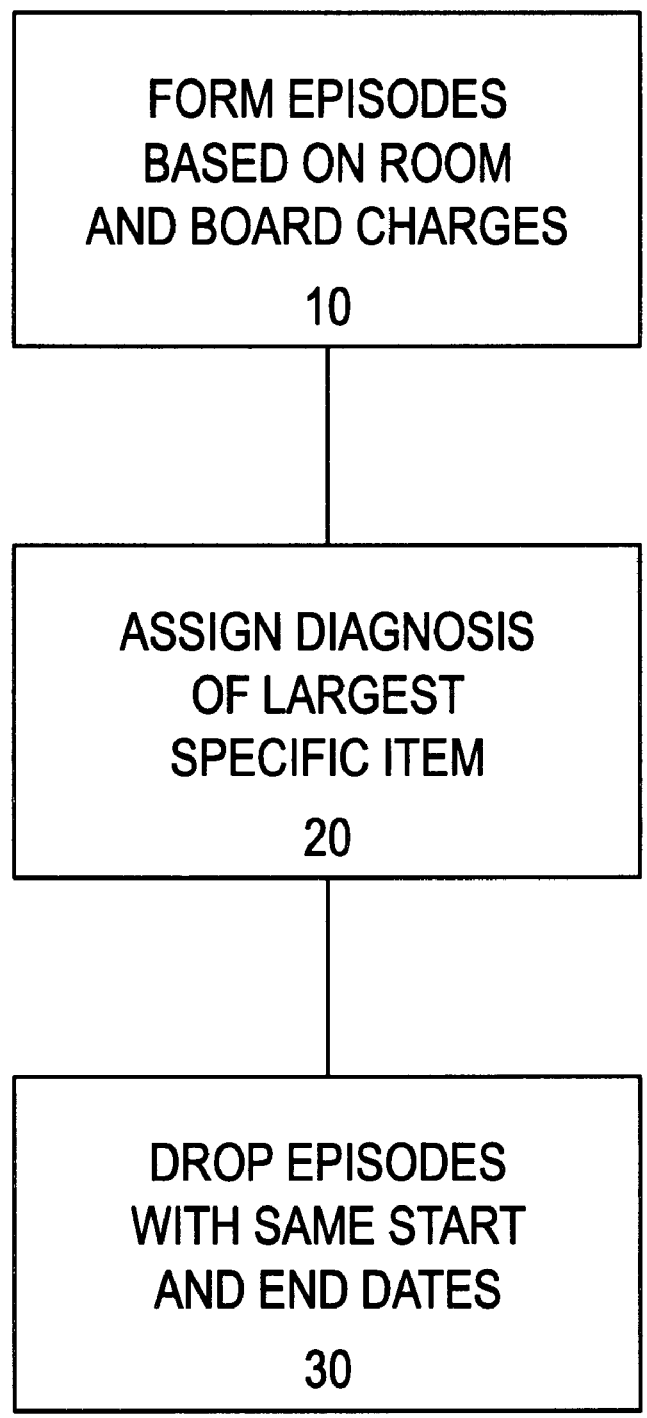
FIG. 1 is a flow diagram showing the analysis of inpatient episodes in accordance with the invention.

In evaluating the medical claims/encounter data, certain types of claims, especially inpatient and outpatient stays, are ordinarily attributable to a single medical condition, regardless of the fact that the ICD.9 codes on the various items of the stay may not consistently show the same ICD.9 code. As illustrated in FIG. 1, the inpatient claims data is first analyzed to form inpatient episodes, i.e., to group all of the claims of an inpatient stay together coded on the basis of the most likely medical condition that caused the inpatient stay.

A multi-step process is used to determine the likely medical condition. First, intermittent room and board claims for the inpatient stay are analyzed (10) to determine the start date and the end date of the stay. The largest room and board item between the start date and the end date is analyzed to determine whether that charge has been assigned a specific diagnosis code. A diagnosis is determined to be specific if it is marked as such in a Diagnostic Cluster Table (discussed in detail below). Typically, 4 and 5 digit ICD.9 codes are considered specific. If the largest room and board item has a specific diagnosis code, all of the items for the inpatient stay between the start date and the end date are assigned that diagnosis (20).

If the largest room and board item does not have a specific diagnosis, the diagnosis of the largest physician's charge with a specific diagnosis code between the start date and the end date is assigned to all items in that inpatient episode. Finally, any inpatient episodes that have the same start date and end date, i.e., the admission and discharge dates are the same, are eliminated (30) as inpatient episodes (these are outpatient episodes, and are discussed below). Thus, all of the items for each inpatient episode are coded with the diagnosis code that is assumed to be the principal medical condition for the inpatient stay.

Once the inpatient episodes have been identified and assigned diagnoses, outpatient episodes are similarly analyzed. Outpatient episodes are determined to be non-inpatient facility charges. The episode length is always one day for an outpatient episode. As with the inpatient episodes, the diagnosis of the largest outpatient facility item with a specific diagnosis, or alternatively, the largest physician charge item with a specific diagnosis is assigned to all of the items on the outpatient treatment date.

In the invention, related ICD.9 codes are grouped into diagnostic clusters based upon clinical homogeneity with respect to generating a similar clinical response from physicians. The diagnostic cluster methodology is described in Schneeweiss, et al., "Diagnostic clusters: a new tool for analyzing the content of ambulatory medical care", Med Care, 1977;15:1024, the content of which is incorporated herein by reference. The approximately 14,000 ICD.9 codes are preferably mapped to 961 diagnostic clusters, although the number of diagnostic clusters is subject to variation. Table 1 shows a sample diagnostic cluster table for diseases of the blood. As shown in Table 1, certain of the diagnostic clusters have a single ICD.9 code associated therewith, e.g., DC11B.1, as opposed to other diagnostic clusters that have multiple ICD.9 codes associated therewith, e.g., DC11B.3. ICD.9 codes that are associated with only one diagnostic cluster are referred to as specific ICD.9 codes.

TABLE 1

PDG 11B - Diseases of Blood

| DC# | Diagnostic Cluster Description | ICD.9 Codes | Window Period | Rank Order Overall |
|---|---|---|---|---|
| DC11B.1 | Iron deficiency anemias | 280 | 75 days | 526 |
| DC11B.2 | Other deficiency anemias<br>Note: The diagnostic cluster "Vitamin deficiency states" has lack of B12 in it (266.2), which will cause pernicious anemia; thus, this will be a related diagnostic cluster, and will be tracked to this;<br>If present with iron, then roll into iron deficiency anemias above | 281 | 75 days | 501 |
| DC11B.3 | Sickle-cell anemia<br>Level #1 With Respect To 282 | 282.5,2 82.6, 282 | 365 days | 185 |
| DC11B.4 | Thalassemias<br>Level #2 With Respect To 282 track to sickle-cell, if present | 282.4, 282 | 365 days | 187 |
| DC11B.5 | Other hereditary hemolytic anemias<br>Level #3 With Respect To 282 Track first to sickle-cell if present in patient<br>Then, track to thalassemias only if sickle-cell not present | 282._, 282 | 365 days | 513 |
| DC11B.6 | Acquired hemolytic anexnias<br>This will be tracked to other anemias, depending upon what is present | 283 | 60 days | 517 |
| DC11B.7 | Aplastic anemias | 284 | 120 days | 520 |

(The notation "_", e.g. "282_", indicates any subclassification within the specified group, e.g. 282, 282., or 282.xx)

Having processed the inpatient and outpatient medical claims/encounter data so that all of these claims have specific diagnoses associated with the most likely medical condition for the inpatient or outpatient stay, the next step in the data analysis is to build patient treatment episodes (PTE), each of which has an associated diagnostic cluster type. A PTE is defined as all inpatient, outpatient, ambulatory, and miscellaneous services incurred for treating a specific medical condition, i.e., any medical condition for which a diagnostic cluster type exists, within a specific period (or window). The system attempts to attribute each medical claim item incurred in treating each specific medical condition within the window for that medical condition to the PTE associated with that medical condition. This period is based on the maximum number of days between contact with a provider for which follow-up care is still reasonable. If the date of service for an individual's specific medical condition is separated by a longer period than the window period, this date of service is considered the start date for a new episode of care.

For example, assume the window period for acute upper respiratory infections is 30 days. Also, assume that in 1991 an individual incurred medical services for a respiratory infection on January 5, January 17, January 28, August 14, and August 23. Using the definition provided previously, this individual had two episodes of care: episode one started on January 5 and ended on January 28; episode two started on August 14 and ended on August 23. The January 28 and August 14 dates were separated by more than the window period (30 days), resulting in two episodes of care. Each of the diagnostic clusters has a unique window period (see Table 1).

Figure 2A:
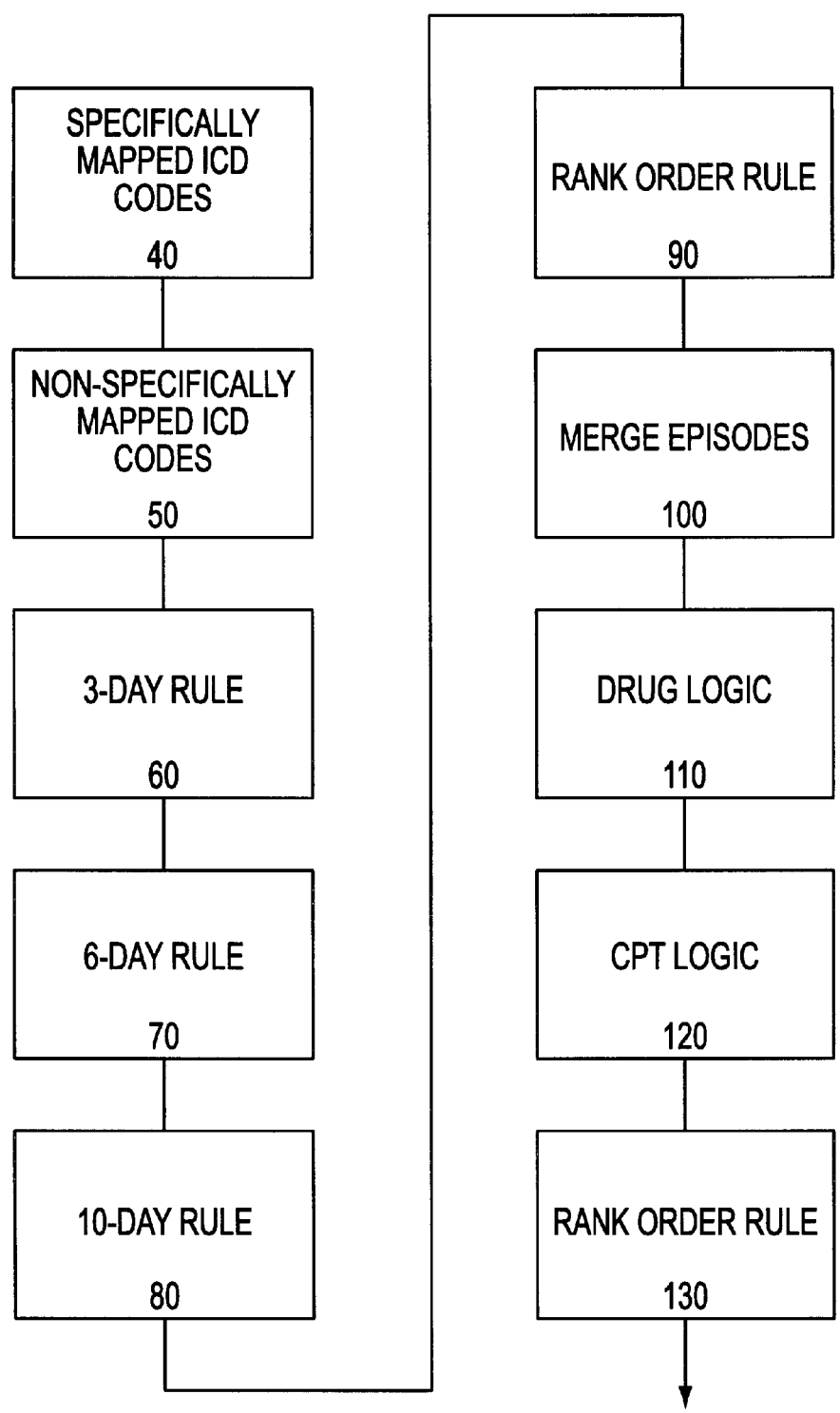
FIGS. 2A–2C is a flow diagram showing the categorization of medical claims into patient treatment episodes in accordance with the invention.
Figure 2B:
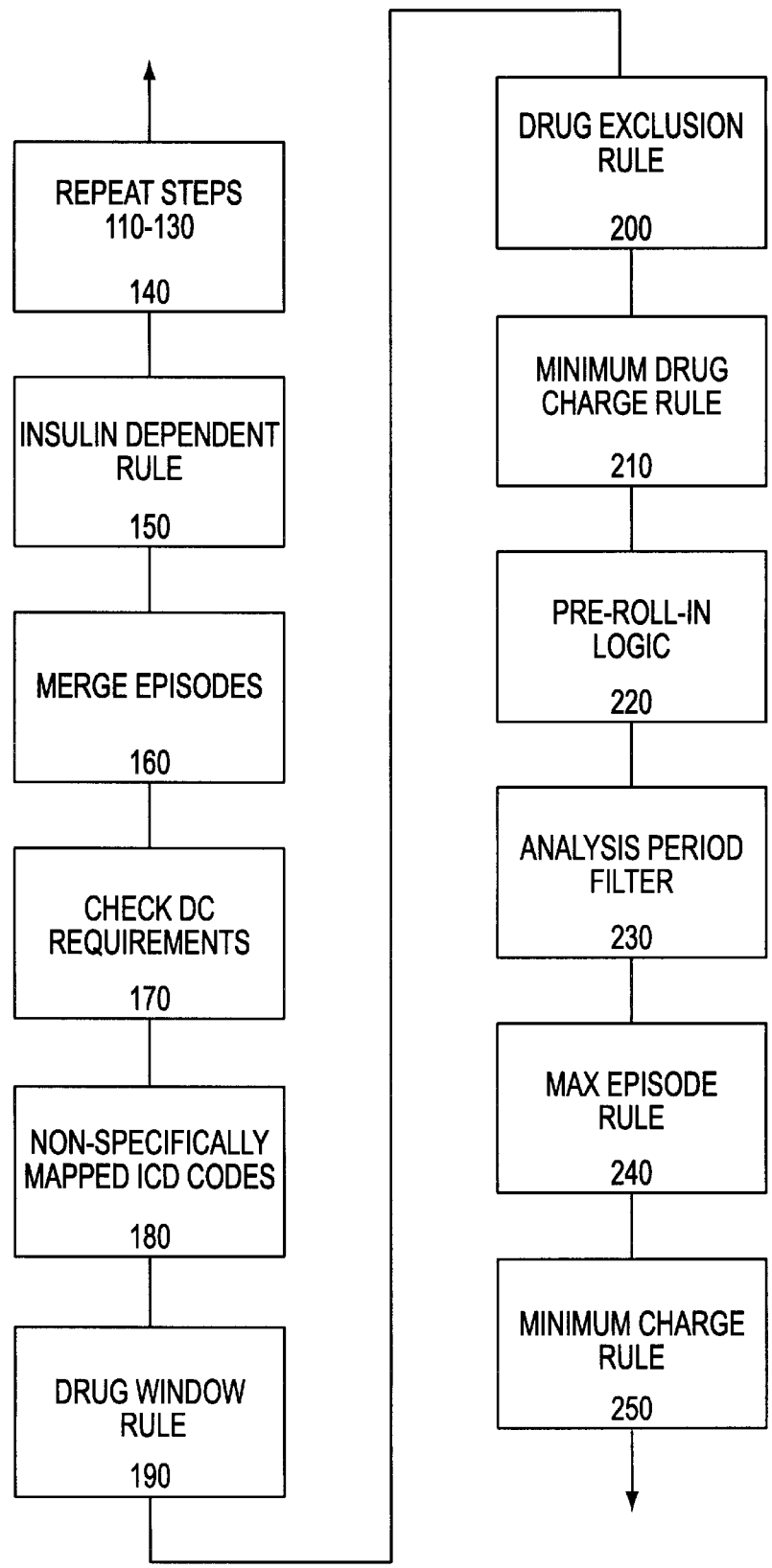
Figure 2C:
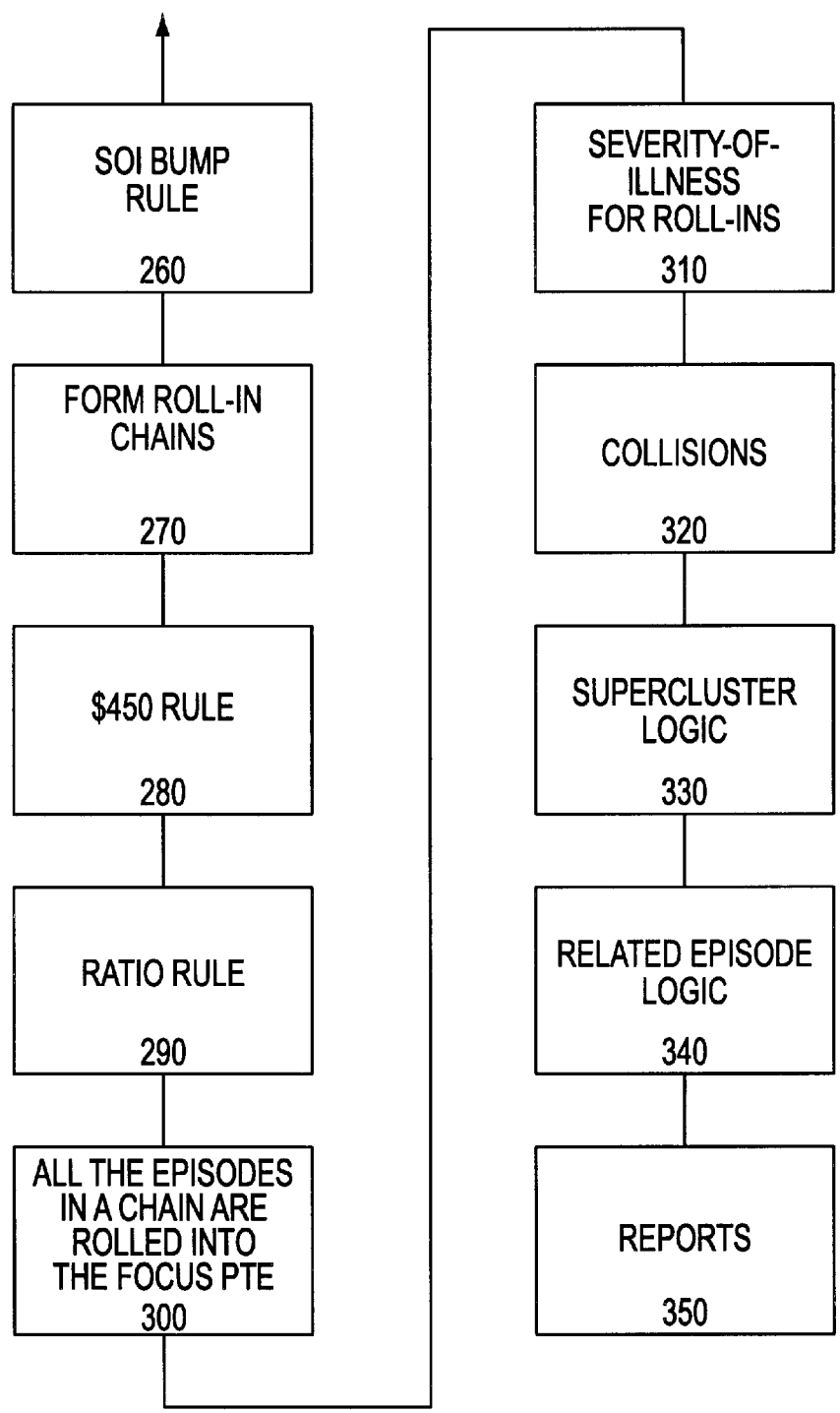

Episodes of care are derived from the diagnosis codes of the submitted medical claims (for ambulatory and miscellaneous claims), and from the diagnosis codes for inpatient and outpatient episodes that were previously derived. As shown in FIG. 2, each item of the medical claims data is first analyzed to determine whether that item has a specifically mapped ICD.9 code (40), i.e., the ICD.9 code of that medical claim/encounter is mapped only to a single diagnostic cluster. A new PTE is formed for each claim that has an ICD.9 code that is mapped to one and only one diagnostic cluster.

Non-Specifically Mapped ICD.9 Codes

The next step in the analysis of the medical claims/encounter data is to analyze items with non-specifically mapped ICD.9 codes (50), i.e., ICD.9 codes that map to more than one diagnostic cluster. For example, in Table 1, diagnostic clusters DC11D.3, DC11B.4, and DC11D.5 all include ICD.9 code 282. Thus, ICD.9 code 282 is non-specifically mapped. For each non-specifically mapped item, the system analyzes each ongoing PTE (episodes are considered ongoing if and only if the episode is active, i.e., within the window period of that episode, on the service date of the claim item) to determine whether the ICD.9 code for that item maps to the diagnostic cluster of any ongoing PTE.

If the item maps to more than one ongoing PTE, the item is mapped to the PTE with the highest level diagnostic cluster with respect to that ICD.9 item For example, referring to Table 1, diagnostic cluster DC11D.3 is indicated as being Level # 1 with respect to ICD.9 code 282, diagnostic cluster DC11B.4 indicates that it is Level # 2 with respect to ICD.9 code 282, and DC11B.5 indicates that it is Level # 3 with respect to ICD.9 code 282. Assuming that a medical claim item has ICD.9 code 282, that item will be assigned to the PTE with the highest level (the lowest Level #) ongoing PTE. If an ongoing PTE is a DC11D.3 diagnostic cluster, any ICD.9 code 282 will be assigned to that PTE. However, if only DC11B.4 and DC11B.5 PTEs are ongoing, the 282 ICD.9 code will be assigned to the PTE corresponding to diagnostic cluster DC11B.4 since that PTE has the highest level with respect to that ICD.9 code.

If for a non-specifically mapped ICD.9 code there are no ongoing PTEs to which that ICD.9 code maps, then the Level # 1 diagnostic cluster for that ICD.9 code will form a new PTE. For example, if a claim item has ICD.9 code 282 and there are no ongoing PTEs corresponding to diagnostic clusters DC11B.3, DC11B.4 and DC11B.5, then a new PTE will be created corresponding to diagnostic cluster DC11B.3, which is the Level # 1 diagnostic cluster with respect to ICD.9 code 282. The various levels for each non-specifically mapped ICD.9 code are established as the most likely candidate diagnostic cluster for the item. Thus, if no ongoing diagnostic clusters are present for a non-specifically mapped ICD.9 code, a new PTE is initiated corresponding to the most likely diagnostic cluster for that ICD.9 code.

A common problem with medical claims/encounter data, especially for ambulatory care claims, is that the claims are missing or non-specific diagnosis codes or have diagnostic codes that were incorrectly entered by the physician or physician office staff. Because episodes of care are diagnosis-code driven, ambulatory claims without a diagnosis code will not appear in any episode of care unless a valid diagnosis code can be assigned to the claims. In order to overcome this problem, a multi-step process is used to assign a diagnosis code to each claim with a missing value.

NDAY Rules

The NDAY rules, i.e., the 3-day (60), 6-day (70), and 10-day (80) rules, attempt to assign diagnoses to claims based on the assumption that treatments for an episode will generally occur near to the time that the diagnosis for the episode is made. Each NDAY rule looks forward and/or backward a set number of days ("N") from a claim lacking a diagnosis searching for a claim containing a diagnosis. If a claim containing a diagnosis is found, its diagnosis is assigned to the claim lacking a diagnosis and the claim lacking a diagnosis is placed in the PTE associated with the claim containing a diagnosis.

As shown in Table 1, each diagnostic cluster is assigned an overall rank that measures the relative resource intensity on an epidemiological scale, relative comorbidity, and clinical significance of the cluster relative to the other clusters. For example, myocardial infarction will obviously have an overall higher rank than a broken arm due to its greater resource intensity, comorbidity and clinical significance.

If, in looking forward and/or backward from a claim lacking a diagnosis more than one claim with a diagnosis is found, the diagnosis of the claim belonging to the highest rank PTE is selected, and the claim is placed in that PTE. The rules are preferably applied in the following order until a diagnosis is found (directions are relative to the claim missing a diagnosis): i) look 3 days backward; ii) look 3 days forward; iii) look 6 days backward; iv) look 6 days forward; and v) look 10 days backward.

The rule does not look 10 days forward, which may result in too many drug claims being misclassified because it is rare for a drug to be prescribed between 6 and 10 days prior to a patient actually going to a physician to obtain a diagnosis, although a 10 day look forward may be implemented, if desired. The purpose of the NDAY rule is to supply missing diagnosis codes to medical claims missing such codes based upon treatment containing a diagnosis code within predetermined periods of time. Accordingly, it will be appreciated that these periods of time may be varied, and that such variations are within the scope of the invention. Moreover, if these periods are varied to include, for example, only a single time period, e.g., 3 days, 5 days, etc., such variations are also within the scope of the invention.

Rank Order Rule

Following application of the NDAY rules, the rank order rule (90) attempts to assign claims that still have missing or non-specific diagnoses to the highest ranked ongoing episode. The assumption supporting this rule is that the most resource intensive episode will typically generate the most claims. The resource intensity of an episode is determined by the rank assigned to the diagnostic cluster. The rank order rule preferably operates as follows:

```
for each claim with a missing or unspecified diagnosis
    identify the highest ranked ongoing PTE occurring
        when service for this claim was provided;
    assign the diagnosis of the highest ranked ongoing
        PTE to the claim;
    associate the claim with the highest ranked
        ongoing PTE;
endfor.
```

Episode Merging

Figure 3:
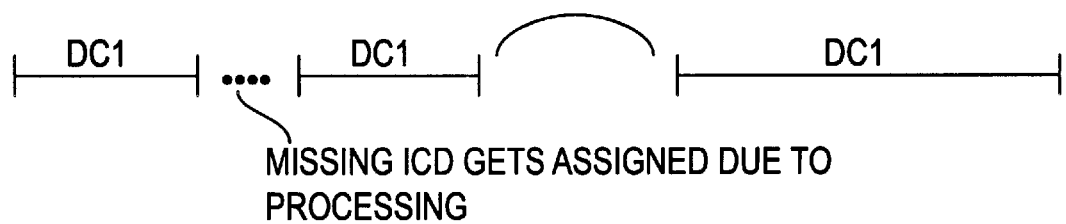
FIG. 3 is a diagram showing operation of the episode merging rule.

Following application of the Rank Order Rule, overlapping episodes that have the same diagnostic cluster are merged (100). For example, if treatment for a DC11B.6 PTE (window period 60 days) occurred on June 1, and the next treatment for a DC11B.6 PTE occurred on August 5, these would be considered separate PTEs because the second treatment did not occur within the window period of the first treatment. If, however, while applying the NDAY Rule a prescription drug claim of June 10 with a missing diagnosis code were assigned to the earlier PTE (that terminating on June 1), thereby extending the termination date of that PTE to June 10, the latter PTE would be within the window period of the earlier PTE, and the two should be joined. Thus, episode merging is used to join overlapping episodes resulting from diagnostic cluster assignment to claims with missing or non-specific ICD.9 codes. Episode merging is illustrated in FIG. 3.

Drug Database Rule

Following episode merging, a drug database rule is applied (110) to identify misclassified prescription drug items based upon a prescription drug database. The drug database rule works to improve the diagnosis assigned to drug claims by using information maintained in a clinically valid prescription drug database that is composed of approximately 250 diagnostic clusters and prescription drug GPI codes. Each diagnostic cluster has three columns of prescription drug GPI codes associated therewith, as illustrated in Table 2:

TABLE 2

| | Drug Database Format | | |
|---|---|---|---|
| DC | Column 1 | Column 2 | Column 3 |
| 932 | GPI Code 1 | GPI Code 1 | GPI Code 1 |
| | . | . | . |
| | . | . | . |
| | GPI Code 15 | GPI Code 15 | GPI Code 15 |

Column 1 consists of FDA approved drugs indicated for treating medical conditions incorporated within the diagnostic cluster. Column 2 consists of FDA and/or clinically valid drugs for treating medical conditions incorporated within the diagnostic cluster. Column 3 consists of off-label usage treatments for treating medical conditions incorporated within the diagnostic cluster and prescription drugs used to treat related conditions. Columns 1 and 2 of the drug database preferably have the same precedence. Obviously, the structure of the drug database is subject to variations that will be appreciated by those skilled in the art and that are within the scope of the invention.

The drug database is preferably used for reassignment of diagnosis codes only of prescription drug claims which meet the following criteria: 1) the claim must have a valid GPI code; 2) the claim must not be associated with an inpatient or outpatient episode; 3) the claim must be associated with a patient treatment episode; 4) the original diagnosis assigned to the claim must be either missing or non-specific; and 5) the diagnostic cluster to which the claim is assigned must have been included and clinically validated in the drug database.

If a claim meets the above criteria the drug reassignment logic is applied, preferably using a decision table of the type shown in Table 3. Table 3 is based upon the situation in which three ongoing episodes exist, i.e., episodes A, B, and C, and claim X (which meets the above criteria) is initially in episode A and is being analyzed for possible reassignment.

TABLE 3

Drug Reassignment Decision Table

| Drug X in Drug DB for Episode A | Drug X in Drug DB for Episode B | Drug X in Drug DB for Episode C | Action |
|---|---|---|---|
| No | No | No | Drug stays in A |
| No | Yes; Column 1 of DB | No | Move drug to B |
| No | Yes; column 3 of DB | No | Move drug to B |
| No | Yes; Column 1 of DB | Yes; Column 1 of DB | Move drug to highest ranked episode B or C |
| No | Yes; Column 1 of DB | Yes; Column 2 of DB | Move drug to highest ranked episode B or C |
| No | Yes; Column 1 of DB | Yes; Column 3 of DB | Move drug to B |
| Yes; Column 1 of DB | No | No | Drug Stays in A |
| Yes; Column 1 of DB | Yes; Column 1 of DB | No | Drug stays in A |
| Yes; Column 1 of DB | Yes; Column 2 of DB | No | Drug stays in A |
| Yes; Column 1 of DB | Yes; Column 3 of DB | No | Drug stays in A |
| Yes; Column 2 of DB | Yes; Column 1 of DB | No | Drug stays in A |
| Yes; Column 2 of DB | Yes; Column 2 of DB | No | Drug stays in A |
| Yes; Column 2 of DB | Yes; Column 3 of DB | No | Drug stays in A |
| Yes; Column 3 of DB | Yes; Column 1 of DB | No | Move drug to B |
| Yes; Column 3 of DB | Yes; Column 2 of DB | No | Move drug to B |
| Yes; Column 3 of DB | Yes; Column 3 of DB | No | Drug stays in A |

CPT Logic

The CPT logic rules (120) work to improve the assignment of claim items containing CPT codes using a clinically valid database that is composed of diagnostic cluster codes and the CPT codes which are related thereto. Each diagnostic cluster has a column of CPT codes associated therewith, as illustrated in Table 4:

TABLE 4

CPT Database Format

| DC | CPT Codes |
|---|---|
| 932 | CPT Code 1 |
| | . |
| | . |
| | . |
| | CPT Code N |
| 933 | CPT Code 1 |
| | . |
| | . |
| | . |
| | CPT Code N |

The CPT codes associated with a given diagnostic cluster are preferably ordered arbitrarily so that no precedence is give to any particular CPT code. Obviously, such precedence could be impemented, if desired.

The CPT reassignment logic is only applied to claims which meet the following criteria 1) the claim must have a valid CPT code; 2) the claim must not be associated with a impatient or outpatient episode; 3) the claim must be associated with a patient treatment episode; 4) the original diagnosis assigned to the claim must be either missing or non-specific; and 5) the cluster to which the claim is assigned must have been included and clinically validated in the CPT database.

If a claim meets the above criteria the CPT reassignment logic is applied, preferably using a decision table of the type shown in Table 5. Table 5 is based upon the situation in which three ongoing episodes exist, i.e., episodes A, B, and C, and claim X (which meets the above criteria) is initially in episode A and is being analyzed for possible reassignment.

TABLE 5

CPT Reassignment Decision Table

| CPT on X in CPT DB for Episode A | CPT on X in CPT DB for Episode B | CPT on X in CPT DB for Episode C | Action |
|---|---|---|---|
| No | No | No | Claim stays in A |
| No | Yes | No | Move claim to B |
| No | No | Yes | Move claim to C |
| No | Yes | Yes | Move claim to highest ranked episode B or C |
| Yes | No | No | Claim stays in A |
| Yes | Yes | No | Claim stays in A |
| Yes | No | Yes | Claim stays in A |
| Yes | Yes | Yes | Claim stays in A |

It will be appreciated that the CPT Reassignment Decision Table may be modified in certain respects that will be appreciated by those skilled in the art. For example, the next to last line of Table 5 indicates that if a CPT on claim X is in the CPT database for episodes A and C, claim X will remain in episode A. This is because it is preferred to leave the claim where in episode A since the claim was placed in this episode by some other logic, e.g., the NDAY rules, Rank Rule, etc. Nonetheless, it is foreseen that the logic may be modified to, for example, move claim X to the higher ranked of episodes A and C under these circumstances.

At this point in the claims processing, the rank order rule is preferably applied again (130), followed by the repetition of steps 110–130 (140). It will be appreciated that during the initial application of these steps, certain claims may have been reclassified to other PTEs, thereby extending or reducing the duration of these PTEs. Accordingly, steps 110–130 are repeated in order to attempt to classify remaining claims that have not yet been classified and that may possibly be classified by the rules on the basis of the revised PTE durations.

Insulin Dependent Rule

Often, claims for diabetics are misclassified by physicians to indicate non-insulin-dependent diabetes, when the patient is actually insulin dependent. This will cause a PTE for non-insulin-dependent diabetes to be initiated. In order to correct this error, the system reviews all prescription drug claims to identify whether a claim for insulin has been submitted by the patient. If such a claim were submitted, the diagnostic cluster for the non-insulin-dependent diabetes PTE is changed to insulin-dependent diabetes (150), and all claims under that PTE are similarly modified. Thus, the system checks the claims data for physician errors.

After this step is completed, the system once again merges overlapping PTEs (160) that have the same diagnostic cluster because the durations of the PTEs may have changed during application of the other rules. It will be appreciated that this technique may be extended to other diseases to identify incorrect physician coding.

Check Diagnostic Cluster Requirements

During the previous steps, PTEs have been established for the diagnostic clusters on the basis of individual claims with the appropriate ICD.9 codes to establish such PTEs. However, certain diagnostic clusters include further limitations that are required to maintain a PTE for such diagnostic clusters. For example, in the diagnostic cluster table for intestinal infections shown in Table 6, diagnostic cluster DC2A.1 for cholera indicates that diagnosis code "001" must be present to include diagnosis codes "V01.0" and/or "V02.0" in the cluster. Thus, while V01.0 or V02.0 will be sufficient to trigger this diagnostic cluster, code 001 must be present in the cluster during this test for the other to remain. Similarly, a childbirth PTE will not be considered valid without at least one claim entry corresponding to childbirth itself. Thus, the diagnostic cluster table contains the required ICD.9 codes to maintain each diagnostic clusters, for those clusters that have such requirements. It will be appreciated that may diagnostic clusters do not have any required ICD.9 codes to remain valid (See Table 1). At this point in the processing, the system reviews each claim in each PTE (or at least the PTEs that have particular minimum ICD.9 requirements as indicated in the diagnostic cluster table), and eliminates any PTEs that don't satisfy the ICD.9 requirements in the diagnostic cluster table (170).

TABLE 6

PDG-2: Infectious and Parasitic Diseases
PDG-2A: Intestinal Infections

| DC# | Diagnostic Cluster Description | IDC.9 Codes | Window Period | Rank Order Overall |
|---|---|---|---|---|
| DC2A.1 | Cholera the 001 must be present to include V01.0 and/or V02.0 here, otherwise, ignore | 001, V01.0, V02.0 | 75 days | 383 |
| DC2A.2 | Typhoid and paratyphoid fevers the 002 must be present to include V02.1 here; otherwise, ignore | 002, V02.1 | 75 days | 385 |
| DC2A.3 | Other salmonella infections | 003 | 75 days | 762 |
| DC2A.4 | Shigellosis | 004 | 45 days | 775 |
| DC2A.5 | Other food poisoning | 005 | 45 days | 777 |
| DC2A.6 | Amebiasis the 006 must be present to include V02.2; otherwise, ignore | 006, V02.2 | 60 days | 387 |
| DC2A.7 | Other protozoal intestinal diseases | 007 | 60 days | 405 |
| DC2A.8 | Other infectious diarrhea and gastroenteritis | 008,009 | 60 days | 776 |

Non-Specifically Mapped ICD.9 Codes

Because the previous step may have resulted in some claim items being freed, i.e., disassociated from PTEs, step 50 is rerun (180). For each non-specifically mapped claim, the system analyzes each ongoing PTE to determine whether the ICD.9 code for that item maps to the diagnostic cluster of any ongoing PTE. If the item maps to more than one ongoing PTE, the item is mapped to the PTE with the highest level diagnostic cluster with respect to that ICD.9 item. If there are no ongoing PTEs to which that ICD.9 code maps, then the Level # 1 diagnostic cluster for that ICD.9 code will form a new PTE.

In addition to the Drug Database Rule (discussed in detail above), the system preferably includes several additional rules to better categorize prescription drug claims with their appropriate PTEs, or at least to remove prescription drug claims that were improperly classified (by the prior rules) from the incorrect PTEs.

Drug Window Rule

The drug window rule (190) identifies recurring prescription drugs which were initially mis-assigned to a PTE but would have been assigned to a future chronic episode if the chronic episode had initiated earlier. For example, a diabetic may have purchased insulin prior to a physician's visit that would trigger a diabetes PTE. However, rather than reclassifying the drug to the chronic condition PTE, the rule simply removes the drug claim from the PTE that it is in, and from further processing. This is because under the constraints with which the rule operates, it is likely that the prescription drug claim does not belong in the PTE in which it is classified, but it is not necessarily clear that the prescription drug claim belongs in the PTE for the chronic condition. Accordingly, the rule errs on the side of simply removing the claim from processing.

While for purposes of the invention a chronic condition is generally classified as one having a window period of 365 days, for purposes of this rule, a chronic condition is any condition having a window period of 105 days or more. This is done in order to make the rule more expansive, i.e., to try to cover more drug claims that are misclassified. Obviously, the 105 day period is subject to variation, as will be appreciated by those skilled in the art.

The rule is implemented as follows:

```
for each ambulatory drug in a PTE
    if the drug is not in the drug database for
    the PTE and there exists a future episode
    with a window period of 105 days or greater
    and for which the drug is in the drug
    database; then
        remove the drug from the PTE; do not
        reassign to another PTE
    endif
endfor
```

Drug Exclusion Rule

The drug exclusion rule (200) is used to identify singular purpose drugs that have been assigned to PTEs for which the drug is not used. As previously discussed, assignment of drugs to unrelated episodes occurs during the episoding steps, most often due to the analysis periods (windows) used when performing episoding. For example, insulin is often included in unrelated episodes due to the lack of a PTE generating diabetic claim being present in the early part of an episode analysis period.

The system includes a drug exclusion database of singular purpose, commonly used, drugs which are identified by their 6 digit GPI codes, as shown in Table 7.

TABLE 7

| GPI CLASS | Description | Maximum # of Drugs (N in rule) | Maximum % of drugs (M in rule) |
|---|---|---|---|
| 01 | Penicillins | 2 | 40 |
| 02 | Cephalosporins | 2 | 40 |
| 03 | Macrolide Antibiotics | 2 | 40 |
| 04 | Tetracyclines | 2 | 40 |
| 44 | Antiasthmatics | 2 | 40 |
| 58 | Antidepressants | 2 | 40 |
| 65 | Analgesics - Narcotic | 2 | 40 |
| 66 | Anti-rheumatic | 2 | 40 |
| 24 | Estrogens | 999 | 100 |
| 25 | Contraceptives, Oral | 999 | 100 |
| 26 | Progestins | 999 | 100 |
| 28 | Thyroid | 999 | 100 |
| 55 | Vaginal Products | 999 | 100 |
| 33 | Beta Blockers | 4 | 50 |
| 36 | Antihypertensive | 4 | 50 |
| 37 | Diuretics | 4 | 50 |
| 41 | Antihistamines | 4 | 50 |
| 43 | Cough/Cold | 4 | 50 |
| 49 | Ulcer Drugs | 4 | 50 |

The drug exclusion rule operates as follows:

```
for each prescription drug claim associated with a
PTE
    if the drug database does not associate the
    drug with the PTES diagnostic cluster; and
    the drug is in the drug exclusion database;
    and
    (the drug subclass is used N or less times
    within the PTE, or the drug subclass
    represents less than M % of total ambulatory
    charges); then
        remove the drug claim from the episode;
        and
        mark the drug as being removed for
        future reporting
    endif
endfor
```

The N and M values in the drug exclusion rule are associated with each drug in the drug exclusion database. Illustrative values for N and M are shown in Table 7. It will be appreciated that the purpose of the drug exclusion rule is to remove relatively small drug charges for common drugs from PTEs in which they most likely do not belong. It is presumed that if the drug represents a substantial percentage of the total drug charges in the PTE, or is present in greater than a threshold amount, it quite possibly belongs in the PTE, e.g., because of an off-label use by a physician, and will be left in the PTE.

Minimum Drug Charge Rule

The minimum drug charge rule (210) identifies drugs that were assigned to a PTE but have not been clinically associated with the PTE and do not represent a significant percentage of the total prescription usage for the PTE. The minimum drug charge rule operates as follows:

```
for each ambulatory drug subclass in a PTE
    if the drug is not in the drug database for the
    PTE and the drug subclass represents less than 35%
    of the ambulatory drug charges; then
        remove all drugs in the drug subclass that
        are associated with the PTE
    endif
endfor
```

Obviously, the 35% value is subject to modification, as will be appreciated by those skilled in the art. Moreover, while the rule removes all prescription drugs of the particular subclass from the PTE if the appropriate conditions are met, the rule may be modified in various respects, such as by removing only those drugs in the subclass that are not in the drug database. Table 8 provides an example of the minimum drug charge rule. The example assumes that a PTE exists which has $100 in prescription drug charges.

TABLE 8

| Drug Subclass | Is Rx in Column 1, 2, or 3 of Drug Database | Total Charges of drug subclass | Subclass charges as percent of PTE Rx charges | Include drug subclass with PTE? |
|---|---|---|---|---|
| 100000 | Y | 25 | 25% | Y |
| 300000 | N | 45 | 45% | Y |
| 453000 | N | 5 | 5% | N |
| 528920 | Y | 15 | 15% | Y |
| 832342 | Y | 10 | 10% | Y |

Pre-Roll-In Rules

Figure 4:
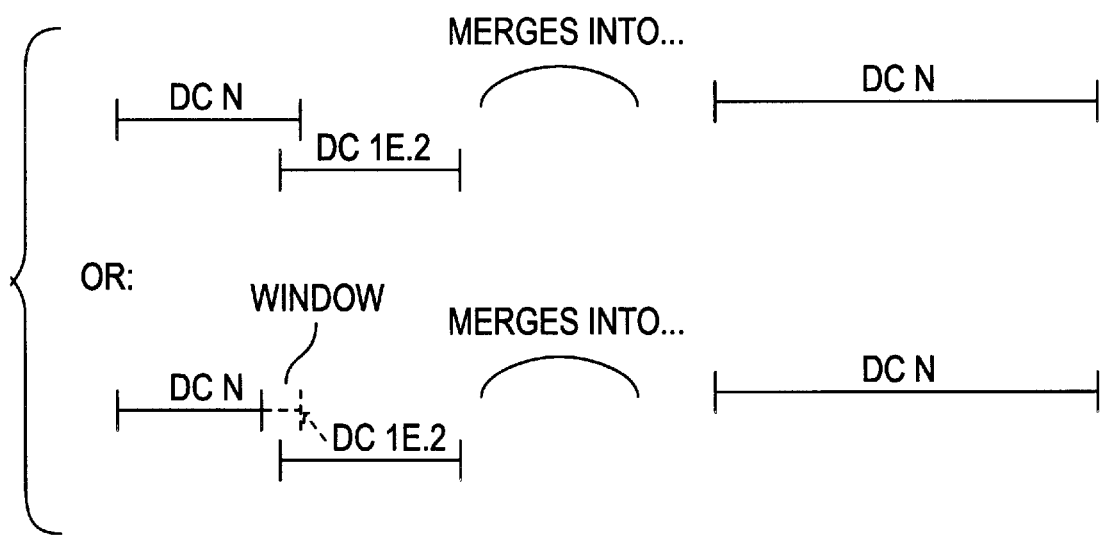
FIG. 4 is a diagram showing the merger of related episodes using the pre-roll-in rules.

The objective of the pre-roll-in rules (220) is to merge PTEs which are created from a symptomatic diagnosis with their underlying conditions. The rules attempt to address non-specific coding patterns of physicians. For example, diagnosis 1E.2 (Medical/Surgical aftercare) will form a PTE, even though it is generally follow-up care for an earlier episode. The pre-roll-in rules will attempt to merge these two episodes together as shown, for example, in FIG. 4.

In general, each diagnostic cluster number is representative of a Primary Diagnostic Group (PDG), a sub-PDG, and a diagnosis. For example, as shown in Table 9, the diagnostic cluster for gout, DC11B.1 is actually representative of PDG11 (immunity disorders and diseases of blood), sub-PDG B (diseases of blood), and diagnosis 0.1 (iron deficiency anemias).

TABLE 9

| DC# | | | DESCRIPTION |
|---|---|---|---|
| 11 | | | IMUNITY DISORDERS AND DISEASES OF BLOOD |
| 11 | A | | Immnunity Disorders |
| 11 | A | 1 | Deficiency of humoral immunity |
| 11 | A | 2 | Deficiency of cell-mediated immunity |
| 11 | A | 3 | Combined immunity deficiency |
| 11 | A | 4 | Other disorder of immune mechanism |
| 11 | B | | Diseases of Blood |
| 1I | B | 1 | Iron deficiency anemias |
| 11 | B | 2 | Other deficiency anemias |
| 11 | B | 3 | Sickle-cell anemia |
| 11 | B | 4 | Thalassemias |
| 11 | B | 5 | Other hereditary hemolytic anemias |
| 11 | B | 6 | Acquired hemolytic anemias |
| 11 | B | 7 | Aplastic anemias |
| 11 | B | 8 | Other anemia disorders |
| 11 | B | 9 | Hemophilia |
| 11 | B | 10 | Other coagulation defects |
| 11 | B | 11 | Purpura |
| 11 | B | 12 | Thrombocytopenia |
| 11 | B | 13 | Other hemorrhagic conditions |
| 11 | B | 14 | Eosinophilia |
| 11 | B | 15 | Diseases of white blood cells |
| 11 | B | 16 | Benign neoplasm of histiocytic, mast, plasma cells |
| 11 | B | 17 | Diseases of spleen |
| 11 | B | 18 | Diseases of blood forming organs |
| 11 | B | 19 | Injury to spleen |
| 11 | B | 20 | Malignant neoplasm of spleen |

The pre-roll-in rules operate in conjunction with a pre-roll-in table of the type shown in Table 10, in which certain diagnostic clusters are related to other PDGs and/or sub-PDGs for the purpose of merging related episodes. The rule analyzes each PTE and operates as follows:

when a PTE is found with a diagnostic cluster in the pre-roll-in rule table (the "target PTE"), perform the following steps until the target PTE is merged into another PTE or each step is completed:

1. loop over each PDG, sub-PDG and diagnostic cluster associated with the target PTE in the pre-roll-in table in precedence order;
   find the highest ranked ongoing PTE with a PDG, sub-PDG and diagnostic cluster in the pre-roll-in table which meets the following conditions:
   PTE initiated prior to the start of the target PTE; diagnostic cluster rank <750; and
   PTE has >$ Cutoff Pass 1 in charges;
   if a PTE is found which meets the conditions, merge the target PTE into PTE under consideration; otherwise, look at the next PDG, sub-PDG and diagnostic cluster in the pre-roll-in table for the target PTE.
2. loop over each PDG, sub-PDG and diagnostic cluster associated with the target PTE in the pre-roll-in table in precedence order;
   find the highest ranked ongoing PTE with a PDG, sub-PDG and diagnostic cluster in the pre-roll-in table which meets the following conditions:
   PTE initiated prior to the start of the target PTE diagnostic cluster rank <750 and
   PTE has >$ Cutoff Pass 2 in charges
   if a PTE is found which meets the conditions, merge the target PTE into PTE under consideration; otherwise, look at the next PDG, sub-PDG and diagnostic cluster in the pre-roll-in table for the target PTE.

The diagnostic cluster rank threshold of 750 in the pre-roll-in rules is established so that only the more important diagnostic clusters are considered for pre-roll-in purposes. Table 10 lists pre-roll-in rules for sample diagnostic clusters. The table columns are defined as follows:

| | |
|---|---|
| DC | Diagnostic cluster no. of target PTE |
| DC Desc | Description of diagnostic cluster type |
| $ Cutoff Pass 1 | Minimum total charges a PTE must have in order for the pre-roll-in diagnostic cluster to be "rolled into" the PTE during the first pass of the pre-roll-in rules |
| $ Cutoff Pass 2 | Minimum total charges a PTE must have in order for the pre-roll-in diagnostic cluster to be "rolled into" the PTE during the second pass of the pre-roll-in rules |
| PDG, Sub-PDG, or DC | identifications of the PDGs, sub-PDGs or diagnostic clusters of PTEs which are potential candidates to accept the target diagnostic cluster. The categories are in precedence order. |
| Exceptions | Exceptions to the previous column. The sub-PDGs and diagnostic clusters listed in this column are not candidates to accept the target diagnostic cluster |

TABLE 10

Pre-Roll-In Table

| DC | DC Desc | $ Cutoff Pass 1 | $ Cutoff Pass 2 | PDG, Sub-PDG, or DC | Exceptions |
|---|---|---|---|---|---|
| 1E.2 | Medical/surgical aftercare | 400 | 100 | Any DC | |
| 11B.14 | Eosinophilia | 250 | 30 | 11B 11A 12 6B 4A 6C 3 2 5C 7E 18A 7E 6A 13A 7D 19A | |
| 12A.9 | Lymphadenitis and lymphadenopathy | 250 | 30 | 12 3 18B 19B18A 2 6A 6C 14B 5B 5C 4A 7A 7E 8D 8E 9 11B 13A 14A 19A 5D | |
| 19A.15 | Fibrositis | 250 | 30 | 20 194 18 17 5D | |
| 21C.9 | Psychogenic physiological state | 250 | 30 | 8 13 18A 4A 6 19 20 7 4B 5B 5C 10C 10D 1OE 14 | |

TABLE 10-continued

Pre-Roll-In Table

| DC | DC Desc | $ Cutoff Pass 1 | $ Cutoff Pass 2 | PDG, Sub-PDG, or DC | Exceptions |
|---|---|---|---|---|---|
| 24A.1 | Coma and stupor | 250 | 30 | 4A 4B 6B 6C 7 8B 11 12 9 10E 15C 21A 21E | 7B 7H |

The definitions of the PDGs and Sub-PDGs in the column entitled "PDG, Sub-PDG, or DC" are as follows:

| DC# | DESCRIPTION |
|---|---|
| 2 | INFECTIOUS AND PARASITIC DISEASES |
| 2 A | Intestinal Infections |
| 3 | HUMAN IMUUNODEFICIENCY VIRUS INFECTIONS |
| 4 | NERVOUS SYSTEM |
| 4 A | Central Nervous System |
| 4 B | Peripheral Nervous System |
| 5 B | Ear |
| 6 C | Nose |
| 5 D | Mouth (Oral Cavity, Salivary Glands, Jaw) |
| 6 | RESPIRATORY SYSTEM |
| 6 A | Upper Respiratory |
| 6 B | Asthma |
| 6 C | Other Lower Respiratory |
| 7 | CIRCULATORY SYSTEM |
| 7 A | Acute Rheuinatic Fever |
| 7 D | Pulmonary Circulation |
| 7 E | Other Forms of Heart Disease |
| 8 | DIGESTIVE SYSTEM |
| 8 A | Esophagus |
| 8 D | Noninfectious Enteritis and Colitis |
| 8 E | Other Disorders of Intestines and Peritoneum |
| 9 | HEPATOBILIARY SYSTEM AND PANCREAS |
| 9 A | Hepatitis |
| 10 C | Other Endocrine Disorders |
| 10 D | Nutritional Deficiencies |
| 10 E | Other Metabolic Disorders |
| 11 | IMMUNITY DISORDERS AND DISEASES OF BLOOD |
| 11 A | Immunity Disorders |
| 11 B | Diseases of Blood |
| 12 | LYMPHATIC AND HEMATOPOIETIC TISSUE |
| 13 | URINARY TRACT AND KIDNEY |
| 13 A | Urinary Tract |
| 14 | REPRODUCTIVE SYSTEM |
| 14 A | Female (Cervix, Vagina, Vulva) |
| 14 B | Female (Pelvic Organ) |
| 15 C | Pregnancy Complications Before Birth |
| 17 | CONGENITAL ANOMALIES |
| 17 A | Anomalies of Nervous System |
| 18 | SKIN, SUBCUTANEOUS TISSUE, AND BREAST |
| 18 A | Skin and Subcutaneous Tissue |
| 18 B | Breast |
| 19 | MUSCULOSKELETAL SYSTEM - DISEASES |
| 19 A | Arthropathies and Related Disorders |
| 19 B | Osteopathies and Chondropathies |
| 20 | MUSCULOSKELETAL SYSTEM - INJURIES |
| 20 A | Skull and Neck |
| 21 | MENTAL DISORDERS |
| 21 A | Organic Psychotic Conditions |
| 21 B | Nonorganic Psychotic Conditions |
| 21 C | Non-psychotic Conditions |
| 21 D | Mental Retardation |
| 21 E | Alcohol and Drug Dependencies |

It will be appreciated that while no diagnostic clusters are listed in the column entitled "PDG, Sub-PDG, or DC", these would be processed in the same manner as PDGs and sub-PDGs in accordance with the pre-roll-in rules above.

Analysis Period Filter

Several additional rules are implemented so as to limit claims analysis to a consistent frame of reference so that objective analysis may be conducted on the claims data. The analysis period filter (230) removes episodes that are outside the specified study period. For example, a typical analysis of claims would cover claims data for a two year period. However, only episodes that begin in the first year are considered, and these are only considered for up to 1 year, or for the duration of the episode, whichever is shorter. Obviously, the period of analysis may be varied, if desired.

Maximum Episode Rule

Similarly, the maximum episode rule (240) trims episodes such that none exceeds 365 days, or whatever study period is in effect. This enable the average annual charge for treatment of the medical condition under consideration to be determined. Obviously, if it desired to study a medical condition over a longer period of time, the rules can be modified or disabled accordingly.

Minimum Charge Rule

It is possible that claims are submitted by physicians wherein the claims have diagnosis codes but are below a minimum total dollar threshold, or even $0.00. These types of claims may trigger PTEs, but are preferably eliminated from further processing. Accordingly, the minimum charge rule (250) removes any episodes that have charges below some other predetermined threshold. In a preferred embodiment, the minimum charge rule is used only to eliminate episodes with $0.00 in total eligible charges.

Severity of Illness Rule

It will be appreciated that the costs of treating certain types of illnesses will vary depending upon the severity of the illness. Thus, it is preferable to include some measure of the severity of the illness in analyzing claims for treatment of the illness. Otherwise any comparison between treatment regimens by different physicians for the same illness would be inaccurate. Generally speaking, severity-of-illness is a stratification within a diagnostic cluster of the relative mortality or morbidity of an episode.

The system includes several severity-of-illness levels, preferably five. The severity-of-illness rule (260) operates to raise the severity-of-illness level on the basis of i) the number of treatments received for the illness; and ii) the types of treatment received. Table 11 shows a severity-of-illness bump table for diseases of blood which indicates the number of treatments required to raise the severity-of-illness level. Table 12 shows a severity-of-illness bump table for diseases of blood which indicates the types of treatments required to raise the severity-of-illness level. The system uses both tables to determine an appropriate severity of illness, as discussed below.

TABLE 11

Severity-Of-Illness Treatment Amounts
PDG-11B: Diseases of Blood

| DC# | | | Diagnostic Center Description | Severity Level 1 | Severity Level 2 | Severity Level 3 | Severity Level 4 | Severity Level 5 |
|---|---|---|---|---|---|---|---|---|
| 11 | B | 1 | Iron deficiency anemias | 1 | 6 | — | — | — |
| 11 | B | 2 | Other deficiency anemias | 1 | 5 | 6 | — | — |
| 11 | B | 3 | Sickle-cell anemia | 1 | 6 | 8 | — | — |
| 11 | B | 4 | Thalassemias | 1 | — | — | — | — |
| 11 | B | 5 | Other hereditary hemolytic anemias | 1 | — | — | — | — |
| 11 | B | 6 | Acquired hemolytic anemias | 1 | 6 | — | — | — |
| 11 | B | 7 | Aplastic anemias | 1 | — | — | — | — |

TABLE 12

Severity-Of-Illness Treatment Types
PDG-11B: Diseases of Blood

| DC# | | | Diagnostic Center Description | Severity Level 1 | Severity Level 2 | Severity Level 3 | Severity Level 4 | Severity Level 5 |
|---|---|---|---|---|---|---|---|---|
| 11 | B | 1 | Iron deficiency anemias | 280_,280 | 280.0 | | | |
| 11 | B | 2 | Other deficiency anemias | 281_,281 | 281.0, 281.1 | 281.3 | | |
| 11 | B | 3 | Sickle-cell anemia | 282.5, 282 | 282.6_ | 282.62 | | |
| 11 | B | 4 | Thalassemias | 282.4, 282 | | | | |
| 11 | B | 5 | Other hereditary hemolytic anemias | 282_ 282 | | | | |
| 11 | B | 6 | Acquired hemolytic anemias | 283_, 283 | 283.0 | | | |
| 11 | B | 7 | Aplastic anemias | 284 | | | | |

For each diagnostic cluster under consideration, the rule accesses the Severity-Of-Illness Treatment Amounts table to determine the number of treatments required to achieve a particular severity level. The rule also accesses the Severity-Of-Illness Treatment Types table to determine the types of treatment required to achieve a particular severity level. For example, with respect to a PTE of diagnostic cluster type DC11B.3, one diagnosis 282.5 or 282 is required to achieve a severity-of-illness of level 1. In order to achieve a severity level 2, it is necessary to have at least 6 treatments in the PTE, wherein at least one of the treatments is of diagnosis 282.6_ (the remaining treatments may have any diagnosis). In order to achieve a severity level 3, the PTE must contain at least 8 treatments, wherein at least one of the treatments is of diagnosis 282.62 (the remaining treatments may have any diagnosis). In a preferred embodiment, the rule is implemented so that it is possible to skip a severity level if the appropriate conditions are met, e.g., the PTE has the correct diagnosis to support level 3, and a sufficient number of treatments to support level 3, although the PTE does not contain the correct diagnosis to support level 2.

Form Roll-In Chains

As mentioned above, there are often variations in coding patterns between physicians treating the same underlying disease. These variations can potentially cause separate PTEs to be generated for the same underlying medical condition, thus fragmenting the reported results. The roll-in rules take related episodes, within a clinically defined group, and roll them into the most severe or most resource intensive episode.

The roll-in process involves the formation of roll-in chains. The relationship of roll-in chains to PTEs is similar to the relationship of PTEs to claim line items. Roll-in diagnostic clusters ("RDCs") define the diagnostic clusters that can make up a chain, as diagnostic clusters define the ICD.9 codes that can make up a PTE.

The diagnostic clusters that make up each RDC are ordered within the RDC in clinical severity order, as shown in Tables 13 and 14, with the most severe episodes being toward the bottom of the tables. When episodes within an RDC occur within the overlapping windows of the episodes, they form a chain which is eventually collapsed into a single episode (270).

Figure 5:
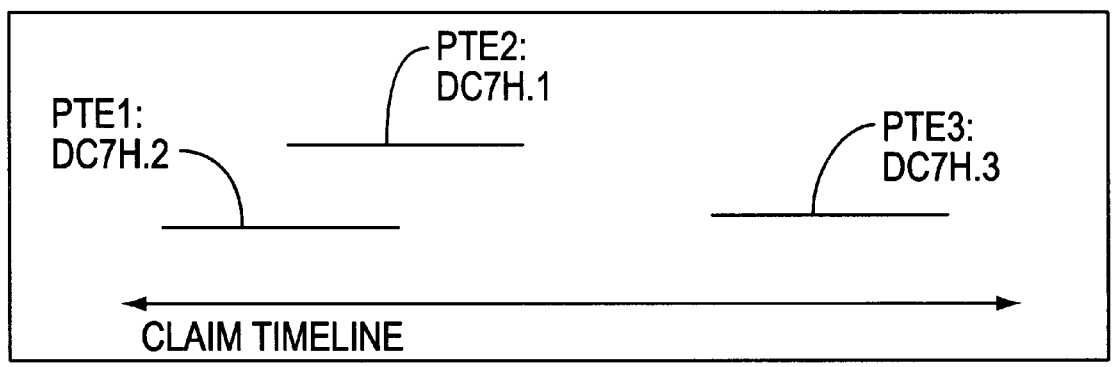
FIG. 5 is a diagram showing the merger of related episodes using the roll-in rules.

FIG. 5 shows operation of the roll-in rules for the situation in which the three episodes listed in Table 13 have been formed. Although all three PTEs are from the same RDC, only PTE1 and PTE2 overlap. They are rolled together to form a single episode of diagnostic cluster 7H.1. PTE3 is too far away from the other episodes to be part of the same roll-in chain.

TABLE 13

RDC for Thrombophlebitis

| DC | DESCRIPTION | ROLL-IN RANK |
|---|---|---|
| 7H.2 | Varicose veins of other sites | |
| 7H.2 | Varicose veins of lower extremity | 2 |
| 7H.1 | Thrombophlebitis | 1 |

During roll-in processing, chains are formed by collecting episodes that are in the same RDCs. At a given point in time, multiple chains, representing different RDCs, may coexist. Episodes in a single chain must also occur within window periods of each other. In order for a PTE to be included in an ongoing roll-in chain, it must start within the window period of the last PTE of the chain. If it does not, the PTE being examined can form a new chain of the same RDC. This guarantees that episodes of acute conditions are not merged to form overextended single episodes.

Table 14 shows sample RDC's.

TABLE 14

Roll-in Diagnostic Clusters

| Roll-In Clusters (In ascending order of importance) | Verbal Description | DC Importance in Roll-In |
|---|---|---|
| | MYONEURAL DISORDERS | |
| 4B.9 | Neuritis upper and lower limbs | |
| 4B.10 | Peripheral neuropathy | |
| 4A.9 | Other demyelinating diseases of CNS | 7 |
| 4A.8 | Multiple sclerosis | 6 |
| 4A.11 | Other paralytic syndromes | 5 |
| 4B.13 | Neurofibromatosis | 4 |
| 4B.11 | Myoneural disorders | 3 |
| 4B.12 | Muscular dystrophies | 2 |
| 4A.10 | Infantile cerebral palsy | 1 |
| | INJURY TO NERVES | |
| 4B.16 LEVEL #1 | Injury to other nerves | |
| 4B.15 | Injury to peripheral nerves pelvic girdle, lower limbs | 1 |
| | INJURY TO CRANIAL AND OTHER NERVES | |
| 4B.16 LEVEL #2 | Injury to other nerves | |
| 4B.2 | Injury to Cranial nerves (except optic) | 1 |
| | INJURY TO PERIPHERAL NERVES | |
| 4B.16 LEVEL #3 | Injury to other nerves | |
| 4b.14 | Injury to peripheral nerves, shoulder, upper arm | 1 |
| | Disorders of the Eye | |
| 17B.1 | Congenital anomalies of eye | 25 |
| 5A.18 | Other disorders of conjunctiva | |
| 5A.20 | Inflammation of eyelid | |
| 5A.17 | Conjunctivitis | 24 |
| 5A.28 | Contusion of eye and adnexa | 23 |
| 5A.29 | External eye injury, foreign body, wound | 22 |
| 5A.19 | Infections of the eyelids | 21 |
| 5A.7 | Disorders of iris and ciliary body | 20 |
| 5A.12 | Lens implant | 19 |
| 5A.32 | Other disorders of eye | 18 |
| 5A.16 | Other disorders of cornea | 17 |
| 5A.15 | Keratitis | 16 |
| 5A.6 | Chorioretinal disorders | 15 |
| 5A.3 | Eye globe prosthesis | 14 |

TABLE 14-continued

Roll-in Diagnostic Clusters

| Roll-In Clusters (In ascending order of importance) | Verbal Description | DC Importance in Roll-In |
|---|---|---|
| 5A.23 | Disorders of orbit | 13 |
| 5A.30 | Internal eye injury, foreign body, wound | 12 |
| 5A.2 | Disorders of globe | 11 |
| 5A.11 | Aphakia | 10 |
| 5A.25 | Disorders of optic nerve | 9 |
| 5A.5 | Other retinal disorders | 8 |
| 5A.9 | Cataract | 7 |
| 5A.33 | Benign neoplasm of eye | 6 |
| 5A.4 | Retinal detachments and defects | 5 |
| 5A.26 | Injury to optic nerve | 4 |
| 5A.34 | Carcinoma in situ of eye | 3 |
| 5A.24 | Orbital floor blow-out | 2 |
| 5A.35 | Malignant neoplasm of eye | 1 |

Generally speaking, when episodes within a RDC have overlapping windows, they form a chain in which the less important PTE is rolled into the more important. Thus, referring to Table 14, a 5A.33, PTE would be rolled into a 5A.4 PTE, if these PTEs were overlapping. Similarly, a 5A.4 PTE would be rolled into a 5A.35 PTE if these were overlapping.

Although not all diagnostic clusters are mapped to RDCs, those that are may be associated with more than one RDC. In such instances, the RDCs will contain a specific ranking with respect to the PTE. For example, referring to Table 14, diagnostic cluster 4B.16 maps to three different RDCs, but includes ranking preferences with respect to these RDCs. For example, if 4B.16, 4B.2, and 4B.14 PTEs are ongoing, the 4B.16 PTE will be rolled into the 4B.2 PTE, since it has a higher preference with respect to that PTE, i.e., Level #2 versus Level #3. This ranking process is similar to the levels given to ICD.9 codes with respect to diagnostic clusters.

$450 Rule

In general, roll-ins occur downward—the most clinically severe episode becoming the dominant identity and absorbing all ongoing episodes in the same RDC. However, in certain cases, a miscoded claim may have created a small very severe PTE. To limit those instances in which this type of PTE would falsely absorb more appropriate PTEs, each diagnostic cluster in an RDC is assigned a priority number (see Table 14, column entitled "DC Importance in Roll-In"). This priority number specifies which diagnostic clusters are eligible to become the focus of the roll-in and in what order.

The rules for determining whether a lower priority PTE should be the focus of the roll-in are applied only if the bottom-most PTE, the most clinically severe, has less than $450 in total eligible charges. If the most severe PTE has more than $450 in charges, the less severe PTE is rolled into the more severe PTE, as discussed above (280). If the most severe PTE has less than $450 in charges, it is compared to the other ongoing episodes in the same RDC to determine if the other episodes are significantly more resource intensive and thus should be the focus of the roll-in. Only those diagnostic clusters that have priority numbers are eligible for consideration for a roll-in (e.g., diagnostic cluster 4B.9 is not eligible for such consideration).

Ratio Rules

These rules (290) are applied only if the most severe PTE has less than $450 in charges. First preference for roll-ins is given to those episodes within the same chain (i.e., overlapping PTE's within the same RDC) where the eligible charges of the most severe PTE in the chain is 24% or less of the charges of the PTE under consideration. Therefore, the less important episode must have charges of at least 416% (1/0.24) of the more important episode for the more important episode to be rolled into the less important episode. The most important episode meeting this criteria, if any exists, becomes the focus of the roll-in.

If no episodes meet the 24% comparison bracket, then those that compare at the 31% or less range are considered for second choice consideration. This requires the lower priority episode to have charges of approximately 322% (1/0.31) or more of the magnitude of the first choice episode.

If no other episodes in the same chain meet either the 24% or 31% limits, then the first choice episode, which has less than $450 in charges, remains the focus of the roll-in. In any case, the PTE into which the other PTEs in the chain will be rolled into is considered the "focus PTE" (300). It will be appreciated that the various ratios used in the ratio rule are subject to variations and modifications, as will be appreciated by those skilled in the art.

Severity of Illness

In a preferred embodiment, the severity of illness of the focus PTE is based upon the rank order (see Table 1) of the PTEs involved in the roll-in. The severity-of-illness of the final combined PTE is set to the highest severity-of-illness among PTEs within rank order groups (310). The groups are listed in Table 15.

TABLE 15

Severity-of-Illness Rank Order Groups

| GROUP | RANK ORDER |
|---|---|
| 1 | 1–75 |
| 2 | 76–150 |
| 3 | 151–350 |
| 4 | 351–600 |
| 5 | 601+ |

Within a single roll-in chain, among the PTEs with diagnostic cluster Rank orders within the same group, the highest severity-of-illness takes precedence. Furthermore, the highest ranked group takes precedence.

For example, assuming a roll-in chain with 5 PTEs as shown below:

| PTE | GROUP | DC RANK | Severity-of-Illness |
|---|---|---|---|
| 1 | 1 | 21 | 2 |
| 2 | 1 | 45 | 1 |
| 3 | 2 | 82 | 2 |
| 4 | 2 | 113 | 5 |
| 5 | 5 | 765 | 4 |

Working upward from the bottom of the table, PTE-5 is in severity-of-illness rank group 5 with a severity-of-illness of 4. At this point, this is the best choice. PTE-4 is in higher rank group, and therefore supersedes PTE-5 as the PTE determining the severity-of-illness. PTE-3 does not supersede PTE-4 because it is in the same rank group as PTE-4, and it has a lower severity-of-illness. PTE-2, although it has a lower severity-of-illness than PTE-4, now supersedes it because it is in a higher ranked group. Finally, the severity-of-illness of PTE-1 is chosen as the severity-of-illness for the combined PTE because it has a higher severity-of-illness than the current PTE, and it is within the same (or higher) rank group.

It should be noted that it is possible that, in the process of assigning a severity-of-illness to the final PTE, the PTE may be assigned a severity-of-illness that is greater than that available for its underlying diagnostic cluster. In this event, the severity-of-illness is reduced to that permitted for such a PTE.

It will be appreciated that the assignment of a severity-of-illness to the combined PTE is subject to variation. For example, the final severity-of-illness of the combined PTE may simply be the severity-of-illness of the focus PTE.

Collisions

It is possible that a "collision" may occur if two episodes of the same diagnostic cluster, previously separated by more than the window period, become "bridged" by another episode in the same RDC that is rolled into one of the episodes. In this instance, the two PTEs are preferably merged and the severity-of-illness is the higher of the two is assigned to the combined PTE.

Supercluster Logic

Certain diagnostic clusters represent the combination of two or more other diagnostic clusters. For example, DC8B.2, entitled "PUD/GERD", is a supercluster, being the combination of DC8A.1, "GERD", and DC8B.1, "PUD". During processing, if separate PTEs of GERD and PUD are found to overlap they are merged together to form a PTE of DC8B.2 (330). The identity of the resultant PTE is specified in a supercluster table of the type shown in Table 16, at the intersection of the two diagnostic clusters under consideration. It will be appreciated that superclusters may be implemented for other medical conditions as well that are the logical combination of two or more other diagnostic clusters, e.g., diabetes, hepatitis, vaccinations, AIDS, etc.

TABLE 16

PUD/GERD Superclusters

| | Major | GERD | PUD | PUD/GERD |
|---|---|---|---|---|
| Minor | | 8A.1 | 8B.1 | 8B.2 |
| Heartburn | 24A.24 | 8A.1 | 8B.2 | 8B.2 |
| GERD | 8A.1 | | 8B.2 | 8B.2 |
| PUD | 8B.1 | | | 8B.2 |
| PUD/GERD | 8B.2 | | | |

Related Episode Logic

Given a primary PTE, one or more secondary PTEs can be related to it through various possible relationships including, but not limited to:

1. Secondary PTE is a complicating factor of the primary PTE;
2. Secondary PTE is a comorbidity of the primary PTE; and
3. Secondary PTE is an adverse event of the primary PTE.

The first step in the process is to specify those diagnostic clusters that are related to a given primary diagnostic cluster (340). Once these relationships have been defined, the relatable PTEs are linked by way of the relationship. Amongst other criteria, two PTEs are relatable if they are listed as relatable, and have a specific temporal relationship.

Once a link has been established, it is preferable to allow the secondary PTE to modify the primary PTE. The types of modifications may include, but are not limited to, changes to the:

1. Extent of the primary PTE;
2. severity-of-illness of the primary PTE;
3. diagnostic cluster associated with the primary PTE; and
4. effective charges related to the primary PTE.

Using diabetes as an example, once the complicating factor, comorbidity and adverse effects links have been established to a diabetes episode, it is possible not only to determine the charges associated with treatment of the diabetes, but the additional charges and the prevalence of the complicating factor, comorbidity and adverse effects links.

During processing, all combinations of PTEs for a given member or subscriber are compared against a table listing all relatable diagnostic cluster combinations and the nature of the relationship. This table, may further specify a minimum severity level required of the secondary PTE in order for certain changes to the primary PTE to be made. If a matching pair is found, then the two PTEs are set as being related in the manner specified in the table. It is possible for two PTEs, when their roles of primary versus secondary PTE is reversed, that the type of relationship between them may change as well.

A Related Complications Table of the type shown in Table 17 for diabetes complicating factors, lists those diagnostic clusters that are tracked as being complicating factors of diabetes. The first column lists the diagnostic cluster number. The diagnostic clusters are subdivided into their PDGs, with each of the diagnostic cluster numbers and a brief description identified. A sample ICD.9 code and description is listed for each of the diagnostic clusters.

TABLE 17

Related Complications Table

Diabetes Complicating Factors

|  | Related Diagnostic Cluster Description | Sample ICD.9 Code | ICD.9 Code/Description |
|---|---|---|---|
| PDG-1: PREVENTIVE CARE AND EXAMINATIONS | | | |
| 1A.1 | Routine general medical exam | V70.0 | Gen med ex healthcare facil |
| 1A.3 | Other medical exam | V70.5 | Hlth ex def subpop |
| 1A.7 | Other special exams | V72 | Spec invest/exams |
| 1A.10 | Screening for endocrine and metabolic disorder | V77.1 | Screen for dm |
| 1A.13 | Screening for neurological, eye, ear diseases | V80 | Screen neural eye/ear dis |
| 1A.16 | Dietary surveillance and counseling | V65.3 | Pers seek diet surveil/counsel |
| 1C.3 | History of other diseases | V18.3 | Fam hx oth blood dsrd |
| 1D.4 | Observation for suspected condition | V29.8 | Obs susp con oth/spec |
| 1E.1 | Adjustment of mechanical device | V52.1 | Fitting artif leg |
| PDG-2: INFECTIOUS AND PARASITIC DISEASES | | | |
| 2D.5 | Septicemia | 038 | Septicemia |
| PDG-4: NERVOUS SYSTEM | | | |
| 4A.13 | Headaches | 307.8 | Special symp/synd psychalgia |
| 4A.14 | Other central nervous system diseases | 337.1 | Autonomic neurop in oth dsrd |
| 4B.9 | Neuritis upper and lower limbs | 354.9, 355.9 | Mononeuritis arm NOS Mononeuritis site NOS |
| 4B.10 | Peripheral neuropathy | 356 | Her/idio peripheral neuropathy |
| 4B.11 | Myoneural disorders | 358.1 | Myoneural dsrd myasth synd NEC |
| PDG-5: SENSE ORGANS (EYE, EAR, NOSE, MOUTH) | | | |
| 5A.2 | Disorders of globe | 360, 260.2 | Disorders of globe Degenerative dsrd qlobe |
| 5A.4 | Retinal detachments and defects | 361 | Ret detachment/defect |
| 5A.5 | Other retinal disorders | 362 | Oth retinal disorder |

TABLE 17-continued

Related Complications Table

Diabetes Complicating Factors

|  | Related Diagnostic Cluster Description | Sample ICD.9 Code | ICD.9 Code/Description |
|---|---|---|---|
| 5A.6 | Chorioretinal disorders | 363 | Chorioretinal inflm/scar/dsrd |
| 5A.7 | Disorders of iris and ciliary body | 364.05, 364.5 | Dsrd iris/ciliary bod hypopyon Dagan iris/ciliary bod |
| 5A.8 | Glaucoma | 365 | Glaucoma |
| 5A.9 | Cataract | 366.1B, 366.1 | Hypomature cataract Cataract assoc w/oth disorder |
| 5A.10 | Disorders of vitreous body | 379.2 | Disorder vitreous body |
| 5A.11 | Aphakia | 379.3 | Aphakia oth disorder lens |
| 5A.12 | Lens implant | V43.1 | Repl in NEC |
| 5A.14 | Blindness and visual disturbances | 368.52, 369 | Visual dist deutan defect Blindness/low vision |
| 5A.15 | Keratitis | 370 | Keratitis |
| 5A.16 | Other disorders of cornea | 371 | Corneal opacity/dsrd cornea |
| 5A.23 | Disorders of orbit | 376 | Disorder orbit |
| 5A.25 | Disorders of optive nerve | 377 | Dsrd optic nerve/vis pathways |
| 5A.32 | Other disorders of eye | 379.4 | Dsrd eye anom pupillary func |
| PDG-7: CIRCULATORY SYSTEM | | | |
| 7B.1 | Hypertension | 401, 402 | Essential hypertension Hypertension heart disease |
| 7C.1 | Acute myocardial infarction | 404.91 | Heart/renal htn w/failure NOS |
| 7C.2 | Angina pectoris | 413 | Angina pectoris |
| 7C.3 | Other ischemic heart disease | 411, 412 | Acute/subacute ischemic heart Old myocardial infarction |

Similarly, Table 18 shows an Adverse Effects Table for diabetes which lists the diagnostic clusters that have been determined to cause adverse effects to the disease or disorder of interest (diabetes). The table lists iatrogenic conditions resulting from either medical or prescription drug care for the underlying disease.

TABLE 18

Adverse Effects Table

Diabetes Adverse Effects

|  | Related Diagnostic Cluster Description | Sample ICD.9 Code | ICD.9 Code/Description |
|---|---|---|---|
| PRESCRIPTION DRUG ADVERSE EFFECTS | | | |
| 1C.4 | Allergy to medicinal agents | V14.7 | Hx algy to serum/vacc |
| 18A.14 | Other erythematous condition | 695 | Erythem cond |
| 16A.20 | Urticaria | 708 | Urticaria |
| 18A.22 | Other disorders of skin and subcutaneous tissue | 709 | Oth dsrd skn/aubout tis |
| 23A.2 | Poisoning by hormones | E932.3 | Advrs eff insulin/antidiab ag |
| 23A.15 | Poisoning by other agents | E858.7, E946, E980.4 | Acc poi ags aff skn/muc mem Ag sk/muc/mem oph oto/den dx Pois und acc/ |

TABLE 18-continued

Adverse Effects Table

Diabetes Adverse Effects

| Related Diagnostic Cluster | Description | Sample ICD.9 Code | ICD.9 Code/Description |
|---|---|---|---|
| 23C.15 | Anaphytatic shock | 995 | purp oth dx/med Cer advrs eff NEC |
| 23C.17 | Other hypersensitivity reaction | 995.2 | Adv eff dx med/bio subst NO3 |
| 24A.13 | Loss of appetite | 783.0 | Symp nutr/metab anorexia |
| 24A.14 | Abnormal weight change | 783.1, 783.2 | Symp nutr abn wt gain Symp nutr abn loss wt |
| 24A.23 | Nausea and vomiting | 787 | Symp invol dig sys |
| 24A.24 | Heartburn | 787.1 | Symp dig sys heartburn |
| MEDICAL CARE ADVERSE EFFECTS | | | |
| 7G.4 | Arteriol ambolism and thrombocic | 444 | Arterial embolism/thrombosis |
| 23C.18 | Complication from surgical procedure | E870.2, E874.2 | Acc punc/hem dialy perf NEC Mec fail dialy/perf NEC |

Table 19 shows a sample Comorbidities Table for diabetes which lists a portion of the most resource intensive comorbidities that are tracked back to diabetes. While other comorbidities exist for the disease in question, the comorbidities table is limited to the most resource intensive comorbidities. The comorbidities do not include any diagnostic clusters that have been identified as complications or adverse effects for the disease in question. Furthermore, in order for a particular PTE of a diagnostic cluster type to be tracked to the disease in question, the PTE must have the severity level indicated in the Comorbidities Table.

TABLE 19

Diabetes Comorbidities Table

| Diagnostic Cluster | Description | Severity of Illness |
|---|---|---|
| 20C.15 | Crushing injury of trunk | 2 |
| 20E.12 | Injury to blood vessels of lower extremity | 3 |
| 21A.1 | Alzheimer's disease | 1 |
| 21A.3 | Senile dementia | 3 |
| 21A.4 | Other organic dementias | 3 |
| 21B.3 | Manic depression | 2 |
| 21B.4 | Bipolar depression | 2 |
| 21B.5 | Major depression | 2 |
| 21B.6 | Schizophrenia | 3 |
| 21C.10 | Anorexia nervosa | 1 |
| 21C.11 | Bulimia | 1 |
| 21C.12 | Anorexia and bulimia | 1 |
| 21C.17 | Nonpsychotic disorders due to brain damage | 1 |
| 21E.1 | Alcohol dependence | 2 |
| 21E.2 | Drug dependence | 2 |
| 21E.3 | Alcohol and drug dependence | 1 |
| 22A.1 | Burn of face, head, neck | 3 |
| 22A.2 | Burn of trunk | 4 |
| 22A.5 | Burn of lower limb | 4 |
| 22A.6 | Burn of internal organs | 3 |
| 22A.7 | Burn of multiple sites | 3 |

Reports

Having used the claims data to form PTEs covering the various medical conditions for each patient whose claims are being analyzed, it is possible to generate various types of reports (350) to analyze the data at the network level, the physician level, and the patient level.

At the network level, it is possible to measure the medical condition case-mix of the patients in the network and the resources used to treat these patients. These measures may be used to focus attention on specific disease categories to improve treatment, to define best practice guidelines, to modify physician panels to better match the needs of the networks patients, or to identify specific patients of health care providers for individual action.

At the physician level, it is possible to measure the medical condition case-mix of the patients in the physicians control and the resources used to treat these patients. These measures may be used to focus attention on specific disease categories to improve treatment, to modify the physician's practice pattern, or to identify specific prescription drug prescribing patterns. As indicated above, one shortcoming of conventional claims analysis systems is that it is difficult to relate the overall charges associated with treatment to the "gatekeeper" physician who recommended or oversaw the treatment. Accordingly, assignment rules are implemented for linking such global episodes, which include all inpatient, outpatient, ambulatory, prescription drug, and other miscellaneous claims to the appropriate physician.

One Dollar Rule

This rule is used to examine the effectiveness of an HMO's gatekeeper approach. Under the rule, if a physician incurs at least $1 of all covered charges within the "global" episode of care, the episode of care is associated with that physician. For example, using the $1 rule, an HMO can gain an understanding of the number of episodes of hypertension a primary care physician (PCP) treated versus referring to a specialist.

Twenty Percent Non-Inpatient Charge Rule

Under this rule, a physician must incur at least 20% of the non-inpatient, physician-related covered charges. The 20% or more non-inpatient, physician charge rule optimizes pattern-of-treatment variations because the remaining episode charges are attributable both to tests and procedures ordered by the physician of interest as well as to any specialist referrals.

Fifty Percent Non-Inpatient Charge Rule

Under this rule, a physician must incur at least 50% of the non-inpatient, physician-related covered charges. The 50% or more non-inpatient, physician charge rule ensures the physician was the primary care-giver for the "global" episode of care.

At the patient level, it is possible to identify patients meeting specific disease classifications and practice patterns. For example, all patients with insulin dependent diabetes that have had 2 inpatient hospitalizations. The treatment patterns of these patients may then be analyzed to see if these patients are managed effectively or whether further intervention is appropriate.

Although the present invention has been described in detail with respect to certain embodiments and examples, variations and modifications exist which are within the scope of the present invention as defined in the following claims. More specifically, the invention has been described with respect to certain rules that are utilized to categorize medical claims and to analyze the resultant categorized data. Those skilled in the art will appreciate the these rules are subject to modifications in various respects and that all of the rules may not necessarily be applicable to each possible application of the invention, depending upon the type of data analysis to be done with the categorized claims data and the degree of categorization required for a particular application.

We claim:

1. A system for integrating medical claim/encounter records for comparative analysis, the system comprising:
   A) data storage means for storing medical claims data from one or more data sources, the medical claims data comprising medical claim items, at least a first portion of the medical claim items comprising principal diagnosis codes, and at least a second portion of the medical claim items comprising non-principal diagnosis codes, no diagnosis codes, or incorrect diagnosis codes; and
   B) data processing means comprising
      i) means for forming patient treatment episodes (PTEs) from the principal diagnosis codes, each PTE being of a diagnostic cluster type; and
      ii) means for assigning at least some of the claim items of the second portion of the medical claims to the PTEs on the basis of a relationship between the second portion claim items and the PTEs.

2. The system according to claim 1 wherein the means for assigning at least some of the claim items performs the assignment on the basis of a temporal relationship between the claim items and the PTEs.

3. The system according to claim 1 wherein the means for assigning at least some of the claim items performs the assignment on the basis of a physiological relationship between the claim items and the PTEs.

4. The system according to claim 1 wherein the second portion of the claims comprises drug claims, the system further comprising a drug lookup table for relating drugs to associated diagnostic cluster types, and wherein the means for assigning at least some of the claim items comprises:
   means for identifying drug claims from the second portion of the medical claims; and
   drug logic for identifying misassigned drug claims using the drug lookup table and for reassigning at least some of the drug claims to different PTEs.

5. The system according to claim 4 wherein the drug lookup table further relates drugs to associated diagnostic cluster types in more than one degree of preference, the drug logic further comprising means using the drug lookup table for reassigning at least some of the drug claims to PTEs of diagnostic cluster types having a greater degree of preference.

6. The system according to claim 1 wherein each claim item has an associated treatment date, and each PTE has a predetermined treatment window associated with the diagnostic cluster type for the PTE, the system further comprising a diagnostic cluster lookup table which associates each diagnostic cluster type with associated diagnosis codes, the means for assigning at least some of the claim items assigning each such claim item to a PTE with an ongoing treatment window on the treatment date for that claim item for which the diagnosis code of the claim item is associated with the diagnostic cluster type of the PTE in the diagnostic cluster lookup table.

7. The system according to claim 6 wherein at least some of the diagnostic cluster types are preference ranked with respect to diagnosis codes that are associated with more than one type of diagnostic cluster, and wherein the means for assigning at least some of the claim items assigns each such claim item to a PTE with an ongoing treatment window on the treatment date for that claim item, wherein the PTE is of the diagnostic cluster type having the highest preference rank with respect to the diagnosis code of the claim relative to other PTEs with ongoing treatment windows.

8. The system according to claim 2 wherein a claim item comprising a non-principal diagnosis code, no diagnosis code, or incorrect diagnosis code is assigned the diagnosis code of and assigned to the PTE associated with a claim item with a specific diagnosis code occurring within a predetermined period of time of the claim item comprising a non-principal diagnosis code, no diagnosis code, or incorrect diagnosis code.

9. The system according to claim 8 wherein each diagnostic cluster type has an associated ranking, and wherein a claim item comprising a non-principal diagnosis code, no diagnosis code, or incorrect diagnosis code is assigned the diagnosis code of and assigned to the PTE of the claim item with a specific diagnosis code occurring within the predetermined period of time that is associated with the PTE of the highest ranking diagnostic cluster type.

10. The system according to claim 1 wherein each diagnostic cluster type has an associated ranking and treatment window, and each claim item has an associated treatment date, and wherein a claim item comprising a non-principal diagnosis code, no diagnosis code, or incorrect diagnosis code is assigned the diagnosis code of and assigned to the PTE with an ongoing treatment window with the highest ranking diagnostic cluster type associated therewith.

11. The system according to claim 1 wherein each diagnostic cluster type has an associated treatment window, the treatment window for each PTE of each diagnostic cluster type extending from a last treatment in that PTE, and wherein each claim item has an associated treatment date, the system further comprising means for merging PTEs of the same diagnostic cluster type when the treatment windows of the PTEs of the same diagnostic cluster type overlap for forming a merged PTE of the same diagnostic cluster type as the overlapping PTEs, the treatment window of the merged PTE extending from the date of a last treatment in the merged PTE.

12. The system according to claim 11 further comprising means for attempting to reassign at least some of the claim items of the second portion of the medical claims to the PTEs on the basis of the treatment window of the merged PTE.

13. The system according to claim 1 wherein the second portion of the claims comprises claims having CPT codes associated therewith, the system further comprising a CPT lookup table for relating CPT codes to associated diagnostic cluster types, and wherein the means for assigning at least some of the claim items comprises:
   means for identifying CPT claims from the second portion of the medical claims, the CPT claims comprising CPT codes and missing or non-specific diagnosis codes; and
   CPT logic for identifying misassigned CPT claims using the CPT lookup table and for reassigning at least some of the CPT claims into different PTEs.

14. The system according to claim 1 wherein a diagnostic cluster type comprises a required diagnosis associated therewith, the system further comprising means for analyzing each PTE to determine the presence of the required diagnosis for the diagnostic cluster type associated with that PTE, and means for eliminating any PTE without the required diagnosis.

15. The system according to claim 1 further comprising means for identifying PTEs that are clinically related or clinically similar; and
   means for merging such clinically related or clinically similar PTEs.

16. The system according to claim 15 further comprising a clinical relationship lookup table identifying clinically related or clinically similar PTEs.

17. The system according to claim 1 wherein each diagnostic cluster type comprises a predetermined severity of illness relationship which relates a severity of illness associated with a PTE of each diagnostic cluster type to the claim items associated with such PTE, and wherein the system further comprises means for varying the severity of illness associated with each PTE on the basis of the claim items in that PTE in accordance with the severity of illness relationship.

18. The system according to claim 1 further comprising means for identifying PTEs related to treatment of a common underlying condition; and
- means for merging such related PTEs into the most severe or most resource intensive of such related PTEs.

19. The system according to claim 18 further comprising:
- means for determining whether the most severe or most resource intensive episode of such related PTEs is larger than the other such related PTEs by a predetermined threshold; and
- means for merging the most severe or resource intensive PTE into one of the other such related PTEs in the event that the most severe or most resource intensive episode is not larger than the other such related PTEs by the predetermined threshold.

20. The system according to claim 1 further comprising means for identifying combinations of PTEs that when combined are of a different diagnostic cluster type; and means for combining such PTEs into a single PTE of the different diagnostic cluster.

21. The system according to claim 1 wherein a first PTE relates to a second PTE as a complicating factor, a comorbid condition, or an adverse effect of the second PTE; and
- means for linking the first and second PTEs.

22. The system according to claim 1 further comprising means for identifying inpatient, outpatient, and ambulatory claims items.

23. A method of integrating medical claim/encounter records for comparative analysis, the method comprising the steps of:
- A) storing medical claims data from one or more data sources, the medical claims data comprising medical claim items, at least a first portion of the medical claim items comprising principal diagnosis codes, and at least a second portion of the medical claim items comprising non-principal diagnosis codes, no diagnosis codes, or incorrect diagnosis codes;
- B) forming patient treatment episodes (PTEs) from the principal diagnosis codes, each PTE being of a diagnostic cluster type; and
- C) assigning at least some of the claim items of the second portion of the medical claims to the PTEs on the basis of a relationship between the second portion claim items and the PTEs.

24. The method according to claim 23 wherein the step of assigning at least some of the claim items comprises performing the assignment on the basis of a temporal relationship between the claim items and the PTEs.

25. The method according to claim 23 wherein the step of assigning at least some of the claim items comprises performing the assignment on the basis of a physiological relationship between the claim items and the PTEs.

26. The method according to claim 23 wherein the second portion of the claims comprises drug claims, the method further comprising providing a drug lookup table which relates drugs to associated diagnostic cluster types, and wherein the step of assigning at least some of the claim items comprises:
- identifying drug claims from the second portion of the medical claims; and
- identifying misassigned drug claims using the drug lookup table and reassigning at least some of the drug claims into different PTEs.

27. The method according to claim 26 wherein the drug lookup table further relates drugs to associated diagnostic cluster types in more than one degree of preference, the method further comprising the step of using the drug lookup table to reassign at least some of the drug claims into PTEs of diagnostic cluster types having a greater degree of preference.

28. The method according to claim 23 wherein each claim item has an associated treatment date, and each PTE has a predetermined treatment window associated with the diagnostic cluster type for the PTE, the method further comprising providing a diagnostic cluster lookup table which associates each diagnostic cluster type with associated diagnosis codes, the step of assigning at least some of the claim items further comprising assigning each such claim item to a PTE with an ongoing treatment window on the treatment date for that claim item for which the diagnosis code of the claim item is associated with the diagnostic cluster type of the PTE in the diagnostic cluster lookup table.

29. The method according to claim 28 wherein at least some of the diagnostic cluster types are preference ranked with respect to diagnosis codes that are associated with more than one type of diagnostic cluster, and wherein the step of assigning at least some of the claim items comprises assigning each such claim item to a PTE with an ongoing treatment window on the treatment date for that claim item, wherein the PTE is of the diagnostic cluster type having the highest preference rank with respect to the diagnosis code of the claim relative to other PTEs with ongoing treatment windows.

30. The method according to claim 24 wherein a claim item comprising a non-principal diagnosis code, no diagnosis code, or incorrect diagnosis code is assigned the diagnosis code of and assigned to the PTE associated with a claim item with a specific diagnosis code occurring within a predetermined period of time of the claim item without a diagnosis code.

31. The method according to claim 30 wherein each diagnostic cluster type has an associated ranking, and wherein a claim item comprising a non-principal diagnosis code, no diagnosis code, or incorrect diagnosis code is assigned the diagnosis code of and assigned to the PTE of the claim item with a specific diagnosis code occurring within the predetermined period of time that is associated with the PTE of the highest ranking diagnostic cluster type.

32. The method according to claim 23 wherein each diagnostic cluster type has an associated ranking and treatment window, and each claim item has an associated treatment date, and wherein a claim item comprising a non-principal diagnosis code, no diagnosis code, or incorrect diagnosis code is assigned the diagnosis code of and assigned to the PTE with an ongoing treatment window with the highest ranking diagnostic cluster type associated therewith.

33. The method according to claim 23 wherein each diagnostic cluster type has an associated treatment window, the treatment window for each PTE of each diagnostic cluster type extending from a last treatment in that PTE, and wherein each claim item has an associated treatment date, the method further comprising the steps of merging PTEs of the same diagnostic cluster type when the treatment windows of the PTEs of the same diagnostic cluster type overlap and forming a merged PTE of the same diagnostic cluster type as the overlapping PTEs, the treatment window of the merged PTE extending from the date of a last treatment in the merged PTE.

34. The method according to claim 33 further comprising the step of attempting to reassign at least some of the claim items of the second portion of the medical claims to the PTEs on the basis of the treatment window of the merged PTE.

35. The method according to claim 23 wherein the second portion of the claims comprises claims having CPT codes associated therewith, the method further comprising providing a CPT lookup table which relates CPT codes to associated diagnostic cluster types, and wherein the step of assigning at least some of the claim items comprises:

identifying CPT claims from the second portion of the medical claims, the CPT claims comprising CPT codes and missing or non-specific diagnosis codes; and identifying misassigned CPT claims using the CPT lookup table and reassigning at least some of the CPT claims into different PTEs.

36. The method according to claim 23 wherein a diagnostic cluster type comprises a required diagnosis associated therewith, the method further comprising the steps of analyzing each PTE to determine the presence of the required diagnosis for the diagnostic cluster type associated with that PTE, and eliminating any PTE without the required diagnosis.

37. The method according to claim 23 further comprising the step of identifying PTEs that are clinically related or clinically similar; and merging such clinically related or clinically similar PTEs.

38. The method according to claim 37 further comprising the step of providing a clinical relationship lookup table identifying clinically related or clinically similar PTEs.

39. The method according to claim 23 wherein each diagnostic cluster type comprises a predetermined severity of illness relationship which relates a severity of illness associated with a PTE of each diagnostic cluster type to the claim items associated with such PTE, and wherein the method further comprises the step of varying the severity of illness associated with each PTE on the basis of the claim items in that PTE in accordance with the severity of illness relationship.

40. A system for integrating medical claim/encounter records which comprises:

A) data storage means for storing medical claims data, the medical claims data comprising medical claim items, each claim item having an associated treatment date, a first portion of the medical claim items comprising principal diagnosis codes;

B) means for forming initial patient treatment episodes (PTEs) from the principal diagnosis codes, each PTE comprising a predetermined treatment window extending from a last treatment in the PTE;

C) means for assigning at least some of a second portion of the claim items into respective PTEs on the basis of a temporal overlap between the second portion claim items and the treatment windows of the PTEs and extending the treatment window for each respective PTE from the date of treatment of the second portion claim item assigned thereto provided that such date of treatment is later than the prior last treatment in the PTE; and D) means for reanalyzing at least some of the second portion claim items and assigning such claim items to respective PTEs on the basis of a temporal overlap between the second portion claim items and the extended treatment windows of the PTEs.

41. A system for assigning medical claims to a physician which comprises:

A) data storage means for storing medical claims data, the medical claims data comprising medical claim items for treatment of a condition by the physician, and other medical claim items related to treatment of the condition, each medical claim item having a charge;

B) means for forming patient treatment episodes (PTEs) from the medical claim items, a PTE for the condition including claim items for treatment by the physician and other claim items related to treatment of the condition;

C) means for determining whether the charges by the physician in the PTE for the condition exceed a predetermined threshold; and D) means for assigning all of the charges in the PTE for the condition to the physician in the event that the charges by the physician in the PTE for treatment of the condition exceed the predetermined threshold.

* * * * *